US007439336B2

(12) United States Patent
Kornmann et al.

(10) Patent No.: US 7,439,336 B2
(45) Date of Patent: Oct. 21, 2008

(54) PROCESS FOR THE PURIFICATION OF IL-18 BINDING PROTEIN

(75) Inventors: Henri Kornmann, Versoix (CH); Gianni Baer, La Tour-de-Peilz (CH)

(73) Assignee: Ares Trading S.A., Aubonne (CH)

(*) Notice: Subject to any disclaimer, the term of this patent is extended or adjusted under 35 U.S.C. 154(b) by 0 days.

(21) Appl. No.: 11/630,845

(22) PCT Filed: Jun. 27, 2005

(86) PCT No.: PCT/EP2005/053010

§ 371 (c)(1),
(2), (4) Date: Dec. 21, 2006

(87) PCT Pub. No.: WO2006/003134

PCT Pub. Date: Jan. 12, 2006

(65) Prior Publication Data

US 2007/0293658 A1 Dec. 20, 2007

Related U.S. Application Data

(60) Provisional application No. 60/587,296, filed on Jul. 12, 2004.

(30) Foreign Application Priority Data

Jun. 29, 2004 (EP) .................................. 04103047

(51) Int. Cl.
*C07K 1/14* (2006.01)
*C07K 1/20* (2006.01)
(52) U.S. Cl. .................. 530/412; 530/420; 530/421
(58) Field of Classification Search .................. None
See application file for complete search history.

(56) References Cited

U.S. PATENT DOCUMENTS

| | | | |
|---|---|---|---|
| 4,508,825 | A | 4/1985 | Kim et al. |
| 4,579,661 | A | 4/1986 | Gustafsson et al. |
| 4,591,563 | A | 5/1986 | Paul et al. |
| 4,684,723 | A | 8/1987 | Dove et al. |
| 4,728,613 | A | 3/1988 | Brewer et al. |
| 4,743,550 | A | 5/1988 | Ananthapadmanabhan et al. |
| 5,093,254 | A | 3/1992 | Giuliano et al. |
| 5,139,943 | A | 8/1992 | Heinsohn et al. |
| 5,328,841 | A | 7/1994 | Lorch et al. |
| 5,407,579 | A | 4/1995 | Lee et al. |
| 5,407,810 | A | 4/1995 | Builder et al. |
| 5,907,035 | A | 5/1999 | Guinn |
| 6,437,101 | B1 | 8/2002 | Hayenga et al. |
| 6,454,950 | B1 | 9/2002 | Tjerneld et al. |
| 6,559,284 | B1 | 5/2003 | Ageland et al. |
| 2007/0037734 | A1 | 2/2007 | Rossi et al. |
| 2007/0134761 | A1 | 6/2007 | Chatellard et al. |
| 2007/0196895 | A1 | 8/2007 | Aloni et al. |
| 2007/0258962 | A1 | 11/2007 | Chatellard et al. |
| 2008/0076708 | A1 | 3/2008 | Altarocca et al. |

FOREIGN PATENT DOCUMENTS

| | | |
|---|---|---|
| EP | 0477284 | 8/1995 |
| EP | 1 110 969 A1 | 6/2001 |
| WO | WO 92/07868 | 5/1992 |
| WO | WO 96/23061 | 8/1996 |
| WO | WO 99/09063 A1 | 2/1999 |
| WO | WO 00/68260 A1 | 11/2000 |
| WO | WO 2004/101617 A1 | 11/2004 |
| WO | WO 2005/040384 A1 | 5/2005 |
| WO | WO 2005/049649 A1 | 6/2005 |
| WO | WO 2005/083058 A1 | 9/2005 |
| WO | WO 2006/128908 A1 | 12/2006 |
| WO | WO 2006/131550 A1 | 12/2006 |

OTHER PUBLICATIONS

Altschul, S. F. et al. "Basic Local Alignment Search Tool", *J. Mol. Biol.*, 1990, pp. 403-410, vol. 215.
Altschul, S. F. et al. "Gapped BLAST and PSI-BLAST: a new generation of protein database search programs", *Nucleic Acids Research*, 1997, pp. 3389-3402, vol. 25, No. 17.
Balasubramaniam, D. et al. "Tobacco protein separation by aqueous two-phase extraction", *Journal of Chromatography A*, 2003, pp. 119-129, vol. 989.
Baskir, J. N. et al. "Thermodynamics of the Separation of Biomaterials in Two-Phase Aqueous Polymer Systems: Effect of the Phase-Forming Polymers", *Macromolecules*, 1987, pp. 1300-1311, vol. 20.
Baskir, J. N. et al. "Protein Partitioning Two-Phase Aqueous Polymer Systems", *Biotechnology and Bioengineering*, 1989, pp. 541-558, vol. 34.
Bierau, H. et al. "Direct process integration of cell disruption and fluidised bed adsorption in the recovery of labile microbial enzymes", *Bioseparation*, 2001, pp. 73-85, vol. 10.
Bleier, J. E. et al. "Assembly and Mixing of Two-Stage Aqueous Two-Phase Protein Extractions", *Biotechnol. Prog.*, 2001, pp. 697-702, vol. 17.
Bompensieri, S. et al. "Rapid purification of a lipase from *Acinetobacter calcoaceticus* by temperature-induced aqueous two-phase systems", *Biotechnology Techniques*, Aug. 1998, pp. 611-613, vol. 12, No. 8.
Boschetti, E. et al. "Separation of Antibodies by Liquid Chromatography" In *Handbook of Bioseparations*, 2000, pp. 536-632, Chapter 15, vol. 2 of the Separation Science and Technology Series, Academic Press, San Diego, California, edited by Satinder Ahuja.
Boschetti, E. et al. "Bioprocess Tutorial: Hydrophobic Charge-Induction Chromatography", *Genetic Engineering*, Jul. 2000, pp. 1-4, vol. 20, No. 13.
Cordes, A. et al. "Large-Scale Purification of Formate Dehydrogenase", *Methods in Enzymology*, 1994, pp. 600-608, vol. 228.

(Continued)

*Primary Examiner*—Prema Mertz
(74) *Attorney, Agent, or Firm*—Saliwanchik, Lloyd & Saliwanchik

(57) ABSTRACT

The invention relates to a process for the purification of IL-18 binding protein (IL-18BP) from a fluid using aqueous two-phase partitioning.

17 Claims, 3 Drawing Sheets

OTHER PUBLICATIONS

Costa, M. J. L. et al. "Scale-up of recombinant cutinase recovery by whole broth extraction with PEG-phosphate aqueous two-phase", *Bioseparation*, 2000, pp. 231-238, vol. 9.

Devereux, J. et al. "A comprehensive set of sequence analysis programs for the VAX", *Nucleic Acids Research*, 1984, pp. 387-395, vol. 12, No. 1.

Diamond, A. D. et al. "Effect of Amino Acid Sequence", *In: Peptide and Protein Partitioning in Aqueous Two-Phase Systems*, 1990, American Chemical Society, pp. 52-65.

Dos Reis Coimbra, J. et al. "Continuous separation of whey proteins with aqueous two-phase systems in a Graesser contactor", *Journal of Chromatography A*, 1994, pp. 85-94, vol. 668.

Duarte, M. C. T. et al. "Production and purification of alkaline xylanases", *Bioresource Technology*, 1999, pp. 49-53, vol. 68.

Eiteman, M. A. et al. "Peptide Hydrophobicity and Partitioning in Poly(ethylene glycol)/Magnesium Sulfate Aqueous Two-Phase Systems", *Biotechnol. Prog.*, 1990, pp. 479-484, vol. 6.

Eiteman, M. A. et al. "A model for the prediction of partition coefficients in aqueous two-phase systems", *Bioseparation*, 1991, pp. 31-41, vol. 2.

Fernandes, S. et al. "Affinity Extraction of Dye- and Metal Ion-Binding Proteins in Polyvinylpyrrolidone-Based Aqueous Two-Phase System", *Protein Expression and Purification*, 2002, pp. 460-469, vol. 24.

Grantham, R. "Amino Acid Difference Formula to Help Explain Protein Evolution", *Science*, 1973, pp. 862-864, vol. 185.

Guan, Y. et al. "Studies on the Isolation of Penicillin Acylase from *Escherichia coli* by Aqueous Two-Phase Partitioning", *Biotechnology and Bioengineering*, 1992, pp. 517-524, vol. 40.

Guoqiang, D. et al. "Integration of aqueous two-phase extraction and affinity precipitation for the purification of lactate dehydrogenase", *Journal of Chromatography A*, 1994, pp. 145-152, vol. 668.

Hart, R. A. et al. "Large Scale, In Situ Isolation of Periplasmic IGF-I from *E. coli*", Bio/Technology, Nov. 1994, pp. 1113-1117, vol. 12.

Hatti-Kaul, R. "Aqueous Two-Phase Systems", *Molecular Biotechnology*, 2001, pp. 269-277, vol. 19.

Haynes, C. A. et al. "Thermodynamic Properties of Aqueous Polymer Solutions: Poly(ethylene glycol)/Dextran", *J. Phys. Chem.*, 1989, pp. 5612-5617, vol. 93.

Haynes, C. A. et al. "Separation of Protein Mixtures by Extraction: Thermodynamic Properties of Aqueous Two-Phase Polymer Systems Containing Salts and Proteins", 1989, pp. 463-474, vol. 53.

Johansson, G. et al. "Concentration and purification of β-glucosidase from *Aspergillus niger* by using aqueous two-phase partitioning", *Journal of Chromatography B*, 1998, pp. 161-172, vol. 711.

Kim, S.-H. et al. "Structural requirements of six naturally occurring isoforms of the IL-18 binding protein to inhibit IL-18", *PNAS*, Feb. 1, 2000, pp. 1190-1195, vol. 97, No. 3.

King, R. S. et al. "Molecular Thermodynamics of Aqueous Two-Phase Systems for Bioseparations", *AIChE Journal*, Oct. 1988, pp. 1585-1594, vol. 34, No. 10.

Li, Y. et al. "Protein Purification via Aqueous Two-Phase Extraction (ATPE) and Immobilized Metal Affinity Chromatography. Effectiveness of Salt Addition to Enhance Selectivity and Yield of GFPuv", *Biotechnol. Prog.*, 2002, pp. 1054-1059, vol. 18.

Menge, U. et al. "Purification of Proteins from Cell Culture Supernatants", *Develop. Biol. Standard*, 1987, pp. 391-401, vol. 66.

Minami, N. M. et al. "Separation and purification of glucoamylase in aqueous two-phase systems by a two-step extraction", *Journal of Chromatography B*, 1998, pp. 309-312, vol. 711.

Novick, D. et al. "Interleukin-18 Binding Protein: A Novel Modulator of the Th1 Cytokine Response", *Immunity*, Jan. 1999, pp. 127-136, vol. 10.

Pearson, W. R. "Rapid and Sensitive Sequence Comparison with FASTP and FASTA", *Methods in Enzymology*, 1990, pp. 63-98, vol. 183.

Persson, J. et al. "Purification of protein and recycling of polymers in a new aqueous two-phase system using two thermoseparating polymers", *Journal of Chromatography A*, 1999, pp. 31-48, vol. 864.

Porath, J. et al. "Metal chelate affinity chromatography, a new approach to protein fractionation", *Nature*, Dec. 18, 1975, pp. 598-599, vol. 258.

Porath, J. et al. "Immobilized Metal Ion Affinity Adsorption and Immobilized Metal Ion Affinity Chromatography of Biomaterials. Serum Protein Affinities for Gel-Immobilized Iron and Nickel Ions", *Biochemistry*, 1983, pp. 1621-1630, vol. 22.

Puren, A. J. et al. "Gene expression, synthesis, and secretion of interleukin 18 and interleukin 1β are differentially regulated in human blood mononuclear cells and mouse spleen cells", *Proc. Natl. Acad. Sci. USA*, Mar. 1999, pp. 2256-2261, vol. 96.

Schütte, H. et al. "L-2-hydroxyisocaproate dehydrogenase—A new enzyme from *Lactobacillus confusus* for the stereospecific reduction of 2-ketocarboxylic acids", *Appl Microbiol Biotechnol*, 1984, pp. 167-176, vol. 19.

Schütte, H. et al. "L-Leucine dehydrogenase from *Bacillus cereus*", *Appl Microbiol Biotechnol*, 1985, pp. 306-317, vol. 22.

Suzuki, M. et al. "Affinity Partitioning of Protein A Using a Magnetic Aqueous Two-Phase System", *Journal of Fermentation and Bioengineering*, 1995, pp. 78-84, vol. 80, No. 1.

Tjerneld, F. et al. "Affinity Liquid-Liquid Extraction of Lactate Dehydrogenase on a Large Scale", *Biotechnology and Bioengineering*, 1987, pp. 809-816, vol. 30.

Urushihara, N. et al. "Elevation of Serum Interleukin-18 Levels and Activation of Kupffer Cells in Biliary Atresia", *Journal of Pediatric Surgery*, Mar. 2000, pp. 446-449, vol. 35, No. 3.

Vigers, G. P. A. et al. "Crystal Structure of the Type-I Interleukin-1 Receptor Complexed with Interleukin-1β", *Nature*, Mar. 13, 1997, pp. 190-194, vol. 386.

Pending claims in U.S. Appl. No. 11/916,087, filed Nov. 30, 2007, not yet published.

Pending claims in U.S. Appl. No. 11/915,453, filed Nov. 26, 2007, not yet published.

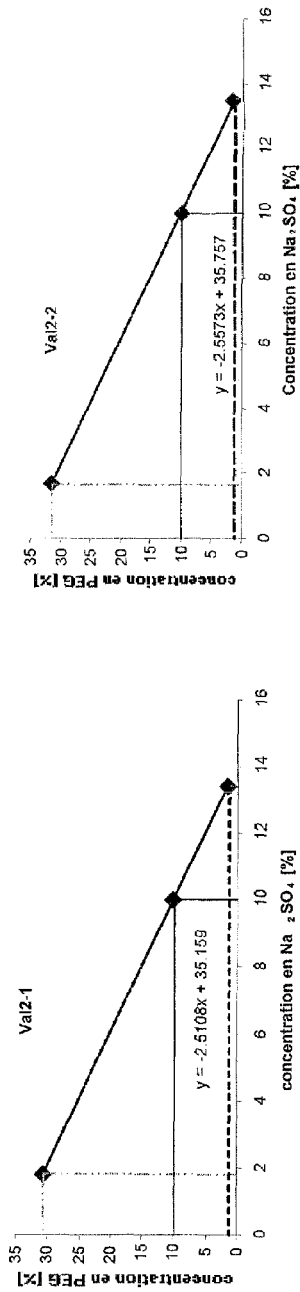
Fig. 2
Fig. 3
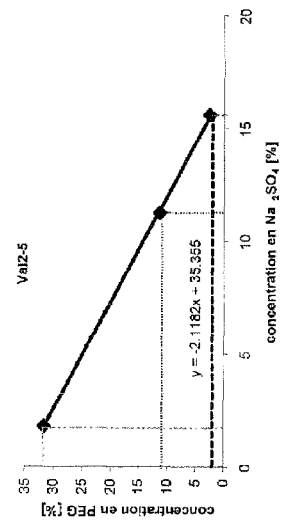
Fig. 4

PROCESS FOR THE PURIFICATION OF IL-18 BINDING PROTEIN

CROSS REFERENCE TO RELATED APPLICATION

This Application is the U.S. national stage application of International Patent Application No. PCT/EP2005/053010, filed Jun. 27, 2005, which claims the benefit of U.S. Provisional Patent Application No. 60/587,296, filed Jul. 12, 2004, the disclosures of which are hereby incorporated by reference in their entireties, including all figures, tables and amino acid or nucleic acid sequences.

FIELD OF THE INVENTION

The present invention is in the field of protein purification. More specifically, it relates to a step for the purification of IL-18 binding protein (IL-18BP) from a fluid using aqueous two phase partitioning.

BACKGROUND OF THE INVENTION

Proteins have become commercially important as drugs that are also generally called "biologicals". One of the greatest challenges is the development of cost effective and efficient processes for purification of proteins on a commercial scale. While many methods are now available for large-scale preparation of proteins, crude products, such as body fluids or cell harvests, contain not only the desired product but also impurities, which are difficult to separate from the desired product. Moreover, biological sources of proteins usually contain complex mixtures of materials.

Biological sources such as cell culture conditioned media from cells expressing a desired protein product may contain less impurities, in particular if the cells are grown in serum-free medium. However, the health authorities request high standards of purity for proteins intended for human administration. In addition, many purification methods may contain steps requiring application of low or high pH, high salt concentrations or other extreme conditions that may jeopardize the biological activity of a given protein. Thus, for any protein it is a challenge to establish an efficient purification process allowing for sufficient purity while retaining the biological activity of the protein.

Protein purification generally comprises at least three phases or steps, namely a capture step, in which the desired protein is separated from other components present in the fluid such as DNA or RNA, ideally also resulting in a preliminary purification, an intermediate step, in which proteins are isolated from contaminants similar in size and/or physical/chemical properties, and finally a polishing step resulting in the high level of purity that is e.g. required from proteins intended for therapeutic administration in human or animals.

Typically, the protein purification steps are based on chromatographic separation of the compounds present in a given fluid. Widely applied chromatographic methods are e.g. gel filtration, ion exchange chromatography, hydrophobic interaction chromatography, affinity chromatography or reverse-phase chromatography.

Aqueous Two-Phase Systems (A2PS) are an alternative to classical chromatographic processes. A2PS processes, have been used in the prior art for the purification of proteins (see Table 1).

TABLE 1

Proteins purified in A2PS

| Protein | Source | MW (kDa) | PI | Yield (%) | Purification factor | References |
|---|---|---|---|---|---|---|
| Xylanase | Bacillus pumilus | 39 | 5.28 | 41 | 57 | (Duarte et al., 2003) |
| β-glucosidase | Aspergillus niger | 91 | 4.69 | 85 | 2 | (Johansson & Reczey, 1998) |
| Lipase | Acinetobacter calcoaceticus | 35 | 6.29 | 68 | 41 | (Bompensieri et al., 1998) |
| Glucoamylase | — | 52 | 4.68 | 96 | 3 | (Minami & Kilikian, 1997) |
| BSA | Bovin | 10 | 5.85 | 95 | — | (Bleier et al., 2001) |
| Cutinase | Sacharomyces cervisiae | 24 | 6.82 | 95 | 5 | (Costa et al., 2000) |
| GFP | Escherishia coli | 27 | 5.67 | 91 | 3.3 | (Li & Beitle, 2002) |
| Lysozyme | Chicken egg white | 2 | 8.00 | 95 | 2.2 | (Balasubramaniam et al., 2003) |

The purification of interferon-beta (IFN-β) from a production medium containing a partially purified serum resulted in a 350-fold purified and up to 10-fold concentrated IFN-β sample with a specific activity of $3\text{-}7.10E10^6$ IU/mg (Menge et al., 1987). However, the application of A2PS for the purification of therapeutic proteins in industrial scale is still limited.

A2PS is based on the partitioning of the target molecule between two immiscible aqueous phases (for instance a PEG/salt system). This system is adapted for proteins extraction because the high water content of both phases (70-80% w/w) means high biocompatibility and low interfacial tension minimizing degradation of the protein. The principle of protein purification by A2PS is e.g. exemplified for the purification of the insulin-like growth factor IGF-1 in U.S. Pat. No. 5,695,958.

The choice of a suitable phase system (polymer/polymer; polymer/salt . . . ) is the key step in a purification process based on A2PS. This system must show a high selective distribution of the target protein between the phases. Examples of couples used for A2PS purification of proteins from various biological sources are illustrated in Table 2.

The composition of aqueous polymer two-phase systems is usually represented in the rectangular form of a phase diagram, as illustrated in FIG. 5, taken from Hatti-Kaul, 2000.

The vertical axis is commonly used for the component, which is enriched in the top phase. Amounts of polymer/salt X, polymer/salt Y and S of water are mixed. The total composition of one mixture is represented by one of the points A1, A2, or A3 on the phase diagram. The mixtures separate into two phases. The compositions of these two phases are represented by the points T and B, which are called nodes and are located at the bimodal line. The bimodal curve is the line separating two domains of compositions: one where the system is monophysic (left and bottom of the curve) and one where phase separation can be observed (top and right of the curve). The line joining the points B and T representing the compositions of the coexisting phases is called a tie line. The points A1, A2, or A3, representing the total mixture must be positioned on the same tie line as the node B and T characterizing the compositions of the coexisting phases originated from these mixtures.

As shown in FIG. 5, mixtures of different total compositions represented by different points on the same tie line give rise to two-phase systems with identical compositions but different volumes of the coexisting phases. The volume ratio of the two phases can be approximated graphically by the ratio of the segment AB (top phase) and AT (bottom phase).

TABLE 2

Examples of protein extraction based on A2PS

| Reference | Enzyme or protein | System used | Origin |
|---|---|---|---|
| (Menge et al., 1984) DE 2943026 | Interferon | PEG-dextran | raw material |
| (Schütte et al., 1984) | D-Lactate dehydrogenase | PEG-phosphate | *Lactobacillus cellubiosus* |
| (Kim et al., 1985) U.S. Pat. No. 4,508,825 | Protease, amylase | PEG-dextran | *Aspergillus orizae* |
| (Schütte et al., 1985) | L-Leucin dehydrogenase | PEG-phosphate | *Bacillus cereus* |
| (Gustafsson et al., 1986) U.S. Pat. No. 4,579,661 | ADH, hexokinase | PEG-phosphate | Yeast |
| (Gustafsson et al., 1986) | Transferrin | PEG-phosphate | Bood plasma |
| (Paul et al., 1986) U.S. Pat. No. 4,591,563 | Dextran-sucrase | PEG-dextran | *Leuconostoc mesenteroides* |
| (van Wijnendaele et al., 1991) EP 0199698 | Hepatitis B antigen | PEG-ammonium sulfate | Yeast |
| (van Wijnendaele et al., 1991) EP 0199698 | Alpha-1-antitrypsin | PEG-ammonium sulfate | Yeast |
| (Dove & Mitra, 1988) U.S. Pat. No. 4,684,723 | Albumin, IgM, IgG, alpha-1-antitrypsin | PEG-phosphate | Blood plasma |
| (Tjerneld & Johansson, 1987) U.S. Pat. No. 6,454,950 | Lactate dehydrogenase | PEG-aquaphase PPT | Pig muscle |
| (Ananthapadmanabhan & Goddard, 1988) U.S. Pat. No. 4,743,550 | Alcaline protease | PEG-sodium sulfate | |
| (Brewer et al., 1988) U.S. Pat. No. 4,728,613 | Protease | PEG-sodium sulfate | whole fermentation bee |
| (Sieron et al., 1994) DD 288837 | Recombinant proteins | PEG-polyvinylalcohol | |
| (Enfors et al., 1992) WO 92/97868 | Human IgG | PEG-phosphate | *Staphylococcus* |
| (Guiliano & Szlag, 1992) U.S. Pat. No. 5,093,254 | Alcohol dehydrogenase (ADH) | PVP-maltodextrin | Baker's yeast |
| (Heinsohne et al., 1992) EP 0 477 284 | Chymosin | PEG-sodium sulfate | *Aspegillus niger* var *awamori* |
| (Kirchberger et al., 1992) DD 298424 | Alkalische phosphatase | PEG-dextran | Calf intestine |
| (Dos Reis Coimbra et al., 1994) | Beta-lactoglobulin | PEG-phosphate | Cheese whey |
| (Dos Reis Coimbra et al., 1994) | Alpha-lactoglobulin | PEG-phosphate | Cheese whey |
| (Cordes & Kula, 1994) | Formate dehydrogenase | PEG-phosphate | *Candida biodinii* |
| (Hart et al., 1994) | IGF | PEG-sodium sulfate | *E. coli* |
| (Lorch et al., 1994) U.S. Pat. No. 5,328,841 | EG | PEG-ammonium sulfate | Cellulase mixture |
| (Builder et al., 1995) U.S. Pat. No. 5,407,819 | IGF-I or mammalian polypeptide | PEG-citrate | *E. coli* |
| (Heinsohne & Hayenga, 1995) EP 0 477 284 | Chymosin | PEG sodium sulfate | Bovine stomach |
| (Lee & Khan, 1995) U.S. Pat. No. 5,407,579 | Hemoglobin | PEG-phosphate | Bovine blood |
| (Braunstein et al., 1995) WO 96/23061 | Different lipases and proteases | Detergents | Different organisms |
| (Guinn, 1997) U.S. Pat. No. 5,907,035 | Recombinant hemoglobin | PEG-magnesium sulfate | *E. coli* |
| (Hayenga et al., 1999) U.S. Pat. No. 6,437,101 | Human growth hormone | PEG-ammonium sulfate | *E. coli* |
| (Tjerneld et al., 2002) U.S. Pat. No. 6,454,950 | BSA | HM-EOPO-water | Blood plasma |
| (Ageland et al., 2003) U.S. Pat. No. 6,559,284 | Apoliprotein A and E | EO sub 30 PO-Reppal PES | *E. coli* |

However, the mechanisms governing the partition of biological materials is still not well understood. It depends on many factors listed in Table 3 below. The most commonly used in current practice are concentration and molecular weight of phase-forming polymers, the type and quantity of the salt and the type and concentration of additives (usually inorganic salts). These factors are generally viewed as the most important to manipulate partitioning of protein to achieve better separation. Therefore, it is extremely difficult to find the appropriate A2PS system for a given protein to be purified from a given source, also because the protein intended for therapeutic use must remain fully functional both in terms of structure (e.g. no aggregation, truncations) and in terms of function.

TABLE 3

Factors capable of steering solute partitioning in aqueous two-phase systems

Type of phase-forming polymers[a]
Molecular weight of phase-forming polymers[a]
Concentrations of phase-forming polymers[a]
Type of additive[b]
Concentration of additive[b]
Temperature
pH
Presence of complex-forming additives[c]
Structural Modification[d]

[a]in aqueous single polymer-salt systems type and concentration of phase-forming salt is the factor equal to those of phase-forming polymer in two-polymer systems.
[b]additive of low molecular weight, such as inorganic salts, urea, etc., with no specific affinity for the solute.
[c]affinity ligands, such as drugs, triazine dyes, organic complexions, fatty acids, etc.
[d]modification by chemical, enzymatic, etc. treatment resulting in elimination, incorporation, or alteration of topography of solvent-accessible moieties in the solute molecule.

Interleukin-18 binding protein (IL-18BP) is a naturally occurring soluble protein that was initially affinity purified, on an IL-18 column, from urine (Novick et al. 1999). IL-18BP abolishes IL-18 induction of IFN-γ and IL-18 activation of NF-κB in vitro. In addition, IL-18BP inhibits induction of IFNγ in mice injected with LPS.

The IL-18BP gene was localized to the human chromosome 11, and no axon coding for a Tran membrane domain could be found in the 8.3 kb genomic sequence comprising the IL-18BP gene. Four isoforms of IL-18BP generated by alternative mRNA splicing have been identified in humans so far. They were designated IL-18BP a, b, c, and d, all sharing the same N-terminus and differing in the C-terminus (Novick et al 1999). These isoforms vary in their ability to bind IL-18 (Kim et al. 2000). Of the four human IL-18BP (hIL-18BP) isoforms, isoforms a and c are known to have a neutralizing capacity for IL-18. The most abundant IL-18BP isoform, isoform a, exhibits a high affinity for IL-18 with a rapid on-rate and a slow off-rate, and a dissociation constant (Kd) of approximately 0.4 nM (Kim et al. 2000). IL-18BP is constitutively expressed in the spleen, and belongs to the immunoglobulin super family. The residues involved in the interaction of IL-18 with IL-18BP have been described through the use of computer modeling (Kim et al. 2000) and based on the interaction between the similar protein IL-1β with the IL-1R type I (Vigers et al. 1997).

IL-18BP is constitutively present in many cells (Puren et al. 1999) and circulates in healthy humans (Urushihara et al. 2000), representing a unique phenomenon in cytokine biology. Due to the high affinity of IL-18BP to IL-18 (Kd=0.4 nM) as well as the high concentration of IL-18BP found in the circulation (20 fold molar excess over IL-18), it has been speculated that most, if not all of the IL-18 molecules in the circulation are bound to IL-18BP. Thus, the circulating IL-18BP that competes with cell surface receptors for IL-18 may act as a natural anti-inflammatory and an immunosuppressive molecule.

IL-18BP has been suggested as a therapeutic protein in a number of diseases and disorders, such as psoriasis, Crohn's Disease, rheumatoid arthritis, psoriatic arthritis, liver injury, sepsis, atherosclerosis, ischemic heart diseases, allergies, etc., see e.g. WO9909063, WO0107480, WO0162285, WO0185201, WO02060479, WO02096456, WO03080104, WO02092008, WO02101049, WO03013577.

The prior art does not describe a purification process of IL-18BP.

SUMMARY OF THE INVENTION

The present invention is based on the development of an efficient purification step for IL-18 binding protein (IL-18BP) that is based on aqueous-two phase partitioning.

Therefore, in a first aspect, the invention relates to a process for the purification of IL-18 binding protein (IL-18BP) from a fluid comprising at least one step comprising an aqueous two-phase system.

A second aspect of the invention relates to the use of an aqueous two-phase system for the purification of IL-18BP from a fluid.

A third aspect of the invention relates to purified IL-18BP obtained by a process according to the invention.

BRIEF DESCRIPTION OF THE DRAWINGS

FIG. 2 shows the Tie-line for conditions Val2-1.

FIG. 3 shows the Tie-line for conditions Val2-2.

FIG. 4 shows the Tie-line for conditions Val2-5.

DETAILED DESCRIPTION OF THE INVENTION

Figure 1:
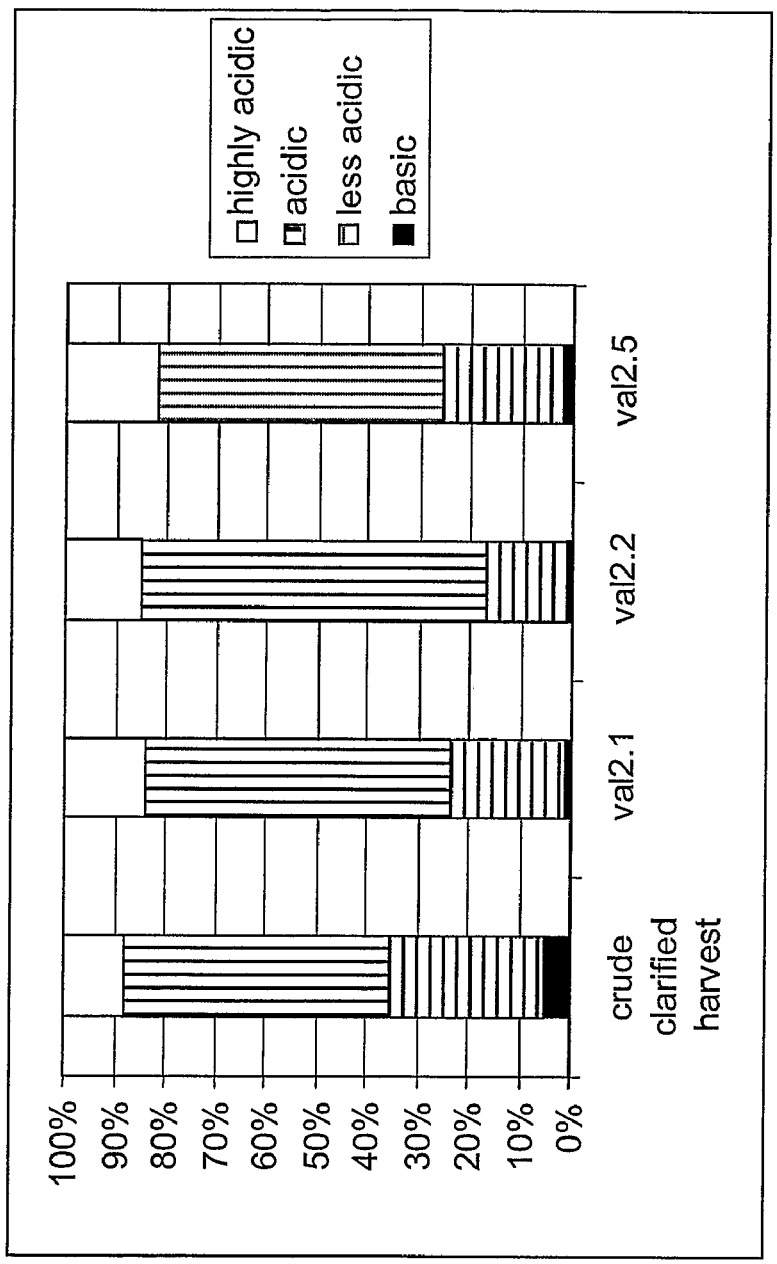
FIG. 1 shows the results from Capillary Zone Electrophoresis (CZE) profiles of leads identified from the statistical model.

The present invention is based on the development of a step for the purification process of IL-18BP.

The invention relates to a process for purifying IL-18BP from a fluid comprising at least one step using aqueous two-phase partitioning. Such an aqueous two-phase system may be used as a single step of purification of IL-18BP. It may also be used as one step among other steps based on other purification methods. It may further be used in multiple steps of the purification process, i.e. two, three or more steps are based on aqueous two phase partitioning. Should the purification process comprise more than one step based on aqueous two-phase system, the individual aqueous two-phase system used may be the same system, or based on different systems, e.g. different polymers, salts, or the like.

In accordance with the present invention, the aqueous two-phase system may be any suitable phase system of two immiscible phases such as e.g. polymer/polymer or polymer/salt phases, as long as the system provides a highly selective distribution of the target protein between the phases.

The polymer can be e.g. dextrin, polyvinyl alcohol, or malt dextrin. Preferably, the aqueous two-phase system comprises a polyethylene glycol (PEG) phase and a salt phase.

The PEG to be used in accordance with the purification process of the invention may have any suitable molecular weight. In a preferred embodiment, the PEG has a molecular weight ranging between about 2,000 and about 12,000, it may be about 3000, or about 4000, or about 5000, or about 6000, or about 7000, or about 8000, or about 9000, or about 10000, or about 11000. It is more preferred that the PEG has a molecular weight of about 10,000.

Suitable salts that may be used in the process of the present invention comprise phosphate salts or sulfate salts. The salt phase may e.g. comprise $KH_2PO_4$. Preferably, the salt phase comprises $(NH_4)SO_4$. Alternatively, the salt phase comprises $(Na_2)SO_4$.

The concentrations of the polymer in the polymer phase may vary. In a preferred embodiment, the initial concentration of the polymer, preferably PEG, is less than about 35% [w/w], less than about 30% [w/w], 29% [w/w], 28% [w/w], 27% [w/w], 26% [w/w], 25% [w/w], 24% [w/w], 23% [w/w], 22% [w/w], 21% [w/w], 20% [w/w], 19% [w/w], 18% [w/w], 17% [w/w], 16% [w/w], 15% [w/w], 14% [w/w], 13% [w/w], 12% [w/w], 11% [w/w], 10% [w/w], 9% [w/w], 8% [w/w], 7% [w/w], 6% [w/w], 5% [w/w], 4% [w/w], 3% [w/w], 2% [w/w], or 1% [w/w].

The concentration of the salt in the salt phase may also vary, in particular depending on the concentration used for the polymer phase. In a preferred embodiment, $Na_2SO_4$ is used at a concentration of less than about 30% [w/w], 25% [w/w], 20% [w/w], 16% [w/w], 15% [w/w], 14% [w/w], 13% [w/w], 12% [w/w], 11% [w/w], 10% [w/w], 9% [w/w], 8% [w/w], 7% [w/w], 6% [w/w], 5% [w/w], 4% [w/w], 3% [w/w], 2% [w/w] or 1% [w/w].

In a highly preferred embodiment of the invention, the concentrations of the two phases are calculated according to the following formula:

$$y=-2.5108x+35.159$$

wherein y=PEG in % [w/w] and x=$(Na_2)SO_4$ in % [w/w].

In a further highly preferred embodiment, the concentrations of the two phases are calculated according to the following formula:

$$y=-2.5573x+35.757$$

wherein y=PEG in % [w/w] and x=$(Na_2)SO_4$ in % [w/w].

In yet a further highly preferred embodiment, the concentrations of the two phases are calculated according to the following formula:

$$y=-2.1182x+35.355$$

wherein y=PEG in % [w/w] and x=$(Na_2)SO_4$ in % [w/w].

In accordance with the present invention, the process is carried out at a pH ranging between pH 4 and 9, it may be carried out at about pH 4, pH 5, pH 6, pH 7, pH 8, or pH 9. Preferably, it is carried about at about pH 5 or at about pH 7.

The process according to the invention may be carried out at any suitable temperature, e.g. at 4° C., 6.5° C., 13° C., 19.5° C., 30° C., but preferably the process is carried out at room temperature.

In a preferred embodiment, the step using an aqueous two-phase system of the invention is a capture step, i.e. an initial step of a purification procedure comprising one or more further steps.

The purification step of the invention may remove >10%, >20%, >30%, >40%>50% or >60% or even >70% of the total contaminants present in the crude material. The yield obtainable with the purification step of the invention may be >50%, >60%, >70% or >80% or even >90%.

In a further preferred embodiment, the process of the invention further comprises one or more additional purification steps.

Preferably, the additional purification steps are selected from metal ion affinity chromatography, ion exchange chromatography, hydrophobic interaction chromatography, and reverse phase chromatography.

Hydrophobic charge-induction chromatography is preferably carried out on a resin having 4-mercaptoethyl-pyridine (MEP) as immobilized legend. MEP-Hypercel® is a resin that is particularly suitable in the frame of the present invention.

The ion exchange chromatography step is preferably carried out using a carboxymethyl (CM)-resin.

The affinity chromatography step is preferably immobilized metal ion affinity chromatography, and chelating sparse is an example for a resin that may be used to carry out this chromatographic step.

Hydrophobic interaction chromatography (HIC) may be carried out on any known HIC resin, such as a resin having alkyl- or aryl-residues as immobilized legend. Butyl-, octal- or phenyl-sparse (agars) are examples of such HIC resins.

A preferred material useful for the reverse phase step is reverse-phase-source 30 RPC.

In a highly preferred embodiment, the purification step of the invention is followed by the steps of:
  a) Subjecting the fluid to immobilized metal ion affinity chromatography;
  b) Subjecting the elate of the metal ion affinity chromatography to hydrophobic charge-interaction chromatography;
  c) Subjecting the elate of the hydrophobic charge-interaction chromatography to ion exchange chromatography;
  d) Subjecting the flow-through of the ion exchange chromatography to hydrophobic interaction chromatography;
  e) Subjecting the elate of the hydrophobic interaction chromatography to reverse phase chromatography.

The fluid is preferably subjected to ultrafiltration or defloration prior to step (a).

While the order of the above steps (a) to (e) is preferred, the steps of the process of the invention may be carried out in any order that leads to a purified protein product.

Step (a) is preferably carried out on a chelating sparse column, such as a chelating sparse fast flow column, having $Zn^{2+}$ ions cheated. Preferably, binding of IL-18BP is carried out at pH 8.5±0.1, preferably in 50 mM sodium phosphate and 0.5 M NaCl having this pH. Elution is preferably carried out at pH 9.0±0.1, e.g. in 0.075 M ammonium acetate having this pH.

Step (b) is preferably carried out on a MEP (4-mercaptoethylpyridine derivative) column, such as MEP HyperCel® (LifeSciences). Binding of IL-18BP is carried out preferably at pH 6.1±0.1, e.g. in PBS 1X+1 NaCl having this pH. Elution is carried out preferably at pH 8.4±0.1, e.g. in with 20 mM phosphate buffer plus 35% propylene glycol, the mixture having pH 8.4±0.1.

Step (c) is preferably carried out on a carboxymethyl-sepharose (CM) column. This is a step in which the flow-through is collected for further purification. This step is based on the fact that in specific circumstances relating e.g. to salt and pH conditions, IL-18BP does not bind to the resin, while impurities bind to it. Preferably, step (c) is carried out at pH 6.0±0.2, for example in the presence of 1 mM MES (N-morpholinoethanesulfonic acid).

Step (d) is preferably carried out on a phenyl sepharose column, such as a Phenyl-Sepharose Fast Flow column. Preferably, binding of IL-18BP is carried out at about pH 9.1±0.2, e.g. in 50 mM sodium borate and 0.9M ammonium soleplate having this pH. The elution from the phenyl-sepharose column is preferably carried out at pH 9.1±0.2 in the presence of an elevated salt concentration, such as in 50 mM sodium borate 9.1±0.2, 0.15 M ammonium soleplate having this pH.

Step (e) is preferably carried out on a Source 30 RPC column. Binding of IL-18BP to the column material is preferably carried out at pH 9.1±0.2, e.g. in 50 mM sodium borate buffer. Elution is preferably carried out using a gradient, IL-18BP eluting around 28-32% of 0.1% trifluoroacetic acid (TFA) in acetonitrile.

It is understood that the conditions described above in connection with steps (a) to (e) of the purification may also be applied when carrying out single steps of the invention, or (sub-)combinations of steps.

In a further preferred embodiment of the present purification process, one or more ultrafiltration steps are performed. Ultrafiltration is e.g. useful for the concentration of the target protein, for buffer exchange, or for the removal of small molecular weight components in the elates resulting from previous chromatographic steps. This ultrafiltration allows to remove organic solvent, TFA and salts from the previous step, to equilibrate the IL-18BP in the bulk buffer and to concentrate the molecule to the desired concentration. Such ultrafiltration may e.g. be performed on ultrafiltration media excluding components having molecular weights below 5 kDa.

Preferably, ultrafiltration is carried out between steps (b) and (c), and/or after step (e). More preferably, two ultrafiltration steps are carried out, one between steps (b) and (c) and one after step (e).

In order to facilitate storage or transport, for instance, the material may be frozen and thawed before and/or after any purification step of the invention.

If the protein purified according to the process of the invention is intended for administration to humans, it is advantageous to further include steps of virus removal. Preferably, a virus removal filtration step is carried out between steps (d) and (e). It is further preferred that a virus removal filtration step is carried out after step (e). More preferably, the process comprises two virus removal steps one of which is carried out between steps (d) and (e), the other of which is carried out after step (e).

The fluid from which IL-18BP is purified in accordance with the present invention is preferably selected from cell culture harvest, cell lysine, cell extract, tissue extract, blood plasma, serum, milk, urine, ascots, plant extract, or a fraction derived from an earlier protein purification step.

The fluid may be unqualified crude cell culture harvest or clarified crude cell culture harvest, and it is preferably derived from Chinese Hamster Ovary (CHO) cells. Clarified crude cell culture harvest refers to a cell culture conditioned medium from which cells and debris has been removed, e.g. by centrifugation or filtration techniques. If unqualified crude cell culture harvest is used as the starting material for the process of the invention, cells and debris are present. As shown in the example below, the purification step of the invention is capable of capturing IL-18BP even from unqualified cell culture harvest that has not been pre-treated.

The CHO cells producing IL-18BP may be grown in suspension, or attached to a surface of a carrier such as e.g. a micro carrier. Preferably, the cells are grown in suspension.

In accordance with the present invention, IL-18BP to be purified may be native, i.e. naturally occurring IL-18BP. It may thus be purified from any natural source or material, such as e.g. from body fluids such as urine.

IL-18BP may also be derived from any animal or human source. Preferably, the IL-18BP to be purified is human, and more preferably it is recombinant IL-18BP. Recombinant IL-18BP may be produced in prokaryotic expression systems, such as in bacterial systems as *Escherichia coli*. It may also be produced in eukaryotic expression systems, such as yeast, insect, or mammalian cells. In accordance with the present invention, it is preferred to express IL-18BP in mammalian cells such as animal cell lines, or in human cell lines. Chinese hamster ovary cells (CHO) are an example of a cell line that is particularly suitable for expression of IL-18BP.

Since IL-18BP is a soluble, secreted protein, it is released into the cell culture supernatant, either by means of its natural signal peptide, or by means of a heterogonous signal peptide, i.e. a signal peptide derived from another secreted protein which may be more efficient in the particular expression system used. The fluid from which IL-18BP is purified is thus preferably cell culture supernatant, such as e.g. CHO-cell supernatant. It is more preferred to purify the protein from the supernatant of cells that were grown in serum-free medium, i.e. in culturing medium not containing serum derived from fetal calf or other animal sources.

The term "IL-18 binding protein" is used herein synonymously with "IL-18BP". This term relates IL-18 binding proteins such as the ones defined in WO 99/09063 or in Novick et al., 1999. The term IL-18BP includes splice variants and/or isoforms of IL-18 binding proteins, as the ones defined in Kim et al., 2000, in particular human isoforms a and c of IL-18BP. The term "IL-18PB", as used herein, further includes muteins, functional derivatives, active fractions, fused proteins, circularly permutated proteins and slats of IL-18BP as defined in WO 99/09063.

The IL-18BP subject to the purification process according to the present invention may be glycosylated or non-glycosylated, it may be derived from natural sources, such as urine, or it may preferably be produced recombinant. Recombinant expression may be carried out in prokaryotic expression systems like *E. coli*, or in eukaryotic, and preferably in mammalian, expression systems.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without changing considerably the activity of the resulting products as compared with the wild type IL-18BP or viral IL-18BP. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes an IL-18BP or encodes a viral IL-18BP (WO9909063) under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetraethyl ammonium chloride (TMAC) instead of SSC. See Ausubel, supra.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990).

Any such mute in preferably has a sequence of amino acids sufficiently duplicative of that of an IL-18BP, or sufficiently duplicative of a viral IL-18BP, such as to have substantially similar activity to IL-18BP. One activity of IL-18BP is its capability of binding IL-18. As long as the mute in has substantial binding activity to IL-18, it can be used in the purification of IL-18, such as by means of affinity chromatography, and thus can be considered to have substantially similar activity to IL-18BP. Thus, it can be determined whether any given mute in has substantially the same activity as IL-18BP by means of routine experimentation comprising subjecting such a mutein, e.g., to a simple sandwich competition assay to determine whether or not it binds to an appropriately labeled IL-18, such as radioimmunoassay or ELISA assay.

In a preferred embodiment, any such mute in has at least 40% identity or homology with the sequence of either an IL-18BP or a virally-encoded IL-18BP homologue, as defined in WO 99/09063. More preferably, it has at least 50%, at least 60%, at least 70%, at least 80% or, most preferably, at least 90% identity or homology thereto.

Muteins of IL-18BP polypeptides or muteins of viral IL-18BPs, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL-18BP polypeptides or proteins or viral IL-18BPs, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cytokine residues. Proteins and muteins produced by such deletions and/or insertions come within the purview of the present invention.

Preferably, the synonymous amino acid groups are those defined in Table 4. More preferably, the synonymous amino acid groups are those defined in Table 5; and most preferably the synonymous amino acid groups are those defined in Table 6.

TABLE 4

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 5

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 6

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-18BP polypeptides or proteins, or muteins of viral IL-18BPs, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising an IL-18BP, or a viral IL-18BP, or a mute in or fragment thereof, fused with another protein, which, e.g., has an extended residence time in body fluids. An IL-18BP or a viral IL-18BP, may thus be fused to another protein, polypeptide or the like, e.g., an immunoglobulin or a fragment thereof.

"Functional derivatives" as used herein cover derivatives of IL-18BPs or a viral IL-18BP, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-18BP, or viral IL-18BPs, and do not confer toxic properties on compositions containing it.

These derivatives may, for example, include polyethylene glycol side-chains, which may mask antigenic sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of an IL-18BP, or a viral IL-18BP, muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-18BP.

The term "salts" herein refers to both salts of carboxyl groups and to acid addition salts of amino groups of IL-18 inhibitor molecule, or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperdine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the IL-18 inhibitor, such as induction of IFN-gamma in blood cells.

The sequences of IL-18BP and its splice variants/isoforms can be taken from WO99/09063 or from Novick et al., 1999, as well as from Kim et al., 2000.

Functional derivatives of IL-18BP may be conjugated to polymers in order to improve the properties of the protein, such as the stability, half-life, bioavailability, tolerance by the human body, or immunogenicity. To achieve this goal, IL18-BP may be linked e.g. to Polyethlyenglycol (PEG). PEGylation may be carried out by known methods, described in WO 92/13095, for example.

Therefore, in a preferred embodiment, the functional derivative comprises at least one moiety attached to one or more functional groups, which occur as one or more side chains on the amino acid residues. An embodiment in which the moiety is a polyethylene glycol (PEG) moiety is highly preferred.

In a further preferred embodiment of the invention, IL-18BP comprises an immunoglobulin fusion, i.e. the inhibitor of IL-18 is a fused protein comprising all or part of an IL-18 binding protein, which is fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of IL-18BP, in particular the binding to IL-18. The fusion may be direct, or via a short linker peptide which can be as short as 1 to 3 amino acid residues in length or longer, for example, 13 amino acid residues in length. Said linker may be a tripe tide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the IL-18BP sequence and the immunoglobulin sequence. The resulting fusion protein has improved properties, such as an extended residence time in body fluids (half-life), increased specific activity, increased expression level, or the purification of the fusion protein is facilitated.

In a preferred embodiment, IL-18BP is fused to the constant region of an Ig molecule. Preferably, it is fused to heavy chain regions, like the CH2 and CH3 domains of human IgG1, for example. The generation of specific fusion proteins comprising IL-18BP and a portion of an immunoglobulin are described in example 11 of WO 99/09063, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomer or multimedia, hetero- or homomultimeric.

In a third aspect, the invention relates to a protein preparation resulting from the process of purification according to the invention. Such protein preparation preferably contains IL-18BP in a purity that is >50%, more preferably >60%, and most preferably >70. The IL-18BP present in this protein preparation has preferably a low content of dimmers and aggregates, preferably no dimmers and aggregates at all. It is further preferred that the extent of truncation of IL-18BP present in the protein preparation of the invention is <10%, it may be <9%, <8%, <7%, <6%, and preferably <5%, or even <4%, <3%, <2%, or <1%.

The IL-18BP that has been purified in accordance with the present invention further preferably has a specific isoform profile, as measured e.g. by capillary zone electrophoresis. It is preferred that the IL-18BP contains less than 5% of basic isoforms, less than 25% of less acidic isoforms, more than 45% of acidic isoforms, and more than 15% of highly acidic isoforms. Isoform classification is as defined in the Example below.

Should further purification steps be used, preferably using the further steps described above, the IL-18BP preparation obtained may contain less than 20% of impurities, preferably less than about 15%, or about 14%, or about 13%, or about 12%, or about 11% of impurities. Preferably, it contains less than about 10%, or about 5%, 3%, 2% or 1% of impurities, or it may be purified to homogeneity, i.e. essentially being free from pertinacious contaminants.

Purified IL-18BP may be intended for therapeutic use, i.e. for administration to patients. If purified IL-18BP is administered to patients, it is preferably administered systemically, and preferably subcutaneously or intramuscularly, or topically, i.e. locally. Rectal or intrathecal administration may also be suitable, depending on the specific use of purified IL-18BP.

For this purpose, purified IL-18BP may be formulated as a pharmaceutical composition, i.e. together with a pharmaceutically acceptable carrier, recipients or the like.

The definition of "pharmaceutically acceptable" is meant to encompass any carrier, which does not interfere with effectiveness of the biological activity of the active ingredient and that is not toxic to the host to which it is administered. For example, for potential administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transversal (e.g. in slow release formulations), intramuscular, intraperitoneal, intravenous, subcutaneous, oral, intracranial, epidural, topical, rectal, and intranasal routes. Any other therapeutically efficacious route of administration can be used, for example absorption through epithelial or endothelial tissues or by gene therapy wherein a DNA molecule encoding the active agent is administered to the patient (e.g. via a vector) which causes the active agent to be expressed and secreted in vivo. In addition, the protein(s) according to the invention can be administered together with other components of biologically active agents such as pharmaceutically acceptable surfactants, recipients, carriers, diluents and vehicles.

For potential (e.g. intravenous, subcutaneous, intramuscular) administration, the active protein(s) can be formulated as a solution, suspension, emulsion or lyophilized powder in association with a pharmaceutically acceptable potential vehicle (e.g. water, saline, dextrose solution) and additives that maintain its tonicity (e.g. manifold) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethyleneglycol (PEG), as described in the PCT Patent Application WO 92/13095.

The therapeutically effective amounts of the active protein(s) will be a function of many variables, including the type of antagonist, the affinity of the antagonist for IL-18, any residual catatonic activity exhibited by the antagonists, the route of administration, the clinical condition of the patient (including the desirability of maintaining a non-toxic level of endogenous IL-18 activity).

A "therapeutically effective amount" is such that when administered, the IL-18 inhibitor results in inhibition of the biological activity of IL-18. The dosage administered, as single or multiple doses, to an individual will vary depending upon a variety of factors, including IL-18 inhibitor pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the inhibition of IL-18 in an individual.

Purified IL-18BP may be used in an amount of about 0.001 to 100 mg/kg or about 0.01 to 10 mg/kg or body weight, or about 0.1 to 5 mg/kg of body weight or about 1 to 3 mg/kg of body weight or about 2 mg/kg of body weight.

In further preferred embodiments, the purified IL-18BP is administered daily or every other day or three times per week or once per week.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, purified IL-18BP can be administered prophylactically or therapeutically to an individual prior to, simultaneously or sequentially with other therapeutic regimens or agents (e.g. multiple drug regimens), in a therapeutically effective amount.

Purified IL-18BP may be used for preparation of a medicament for treatment and/or prevention of a number of diseases or disorders. Such diseases or disorders are preferably IL-18 mediated disorders. In particular, purified IL-18BP may be used for treatment and/or prevention of psoriasis, psoriatic arthritis, Crohn's Disease, inflammatory bowel disease, rheumatoid arthritis, liver injury such as alcoholic liver cirrhosis, sepsis, atherosclerosis, ischemic heart diseases, allergies, in particular delayed-type hypersensitivity, and closed head injury.

In a third aspect, the invention relates to the use of an aqueous two-phase system for the purification IL-18 binding protein (IL-18BP). Preferably, the aqueous two-phase system is used for the capture of IL-18BP from a fluid.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLE

Purification of Recombinant, Human IL-18BP from Serum-free CHO Cell Harvest

In the present example, a purification step based on an aqueous two-phase system for the purification of IL-18PB from a CHO cell harvest has been developed. To this end, the following steps were carried out:

1. Selection of the phase-forming components (couples) to be screened
2. First factorial design experiments. For every single selected couple, all major factors affecting the protein partitioning were screened over a broad experimental space
3. Second factorial design experiments, Only important factors affecting the partitioning of the target protein were screened over a reduced experimental space
4. Leads predicted by the model were experimentally verified.
5. Leads were optimized and fine tuned.
6. Leads were scaled-up to 1-liter scale.

Selection of the Two-phase Forming Components

Different factors were considered for the selection of the phase forming components: (i) process compatibility; (ii) components price; (iii) components availability; (iv) literature data. In terms of process compatibility, price and availability, the couples PEG/salt were appropriate. The PEG/$(NH_4)_2SO_4$, PEG/$KH_2PO_4$ and PEG/$Na_2SO_4$ were selected.

Therefore the three couples studied were:

1. PEG/$(NH_4)_2SO_4$
2. PEG/$KH_2PO_4$
3. PEG/$Na_2SO_4$

First Cycle of Factorial Design Experiments

The aim of this cycle of factorial design experiments was to select the appropriate phase forming components showing extreme protein partitioning.

The experiment used was a central composite design including a $2^{5-1}$ fractional factorial, 10 star points and 2 centre points. The design enabled estimation of all main effects and two-factor interactions and all pure quadratic effects of the experimental factors. Table A summarizes the type of experimental factors and levels considered. It corresponds to 28 experiments per couple selected.

TABLE A

Factors screened in the first cycle of factorial design experiments

| Factor | Level | | | | |
|---|---|---|---|---|---|
| Temperature ° C. | 4 | 6.5 | 13 | 19.5 | 30 |
| pH[a] | 5 | 6 | 7 | 8 | 9 |
| NaCl conc % (w/w) | 0 | 2 | 4 | 6 | 8 |
| PEG Mw | 2000 | | 6000 | | 10000 |
| Tie-line length[a] | −1 | | 0 | | 1 |

[a]Tie-line length is related to phase forming components concentration.

The experimental conditions that were used are described in Tables B, C and D.

TABLE B

Conditions for IL-18BP in PEG/$KH_2PO_4$

| Run Order | NaCl % [w/w] | pH | PEG Mw | Tie-line | $KH_2PO_4$ % [w/w] | PEG % [w/w] | Temp [° C.] |
|---|---|---|---|---|---|---|---|
| 7 | 0.5 | 6 | 2000 | −1 | 10 | 12 | 19.5 |
| 16 | 1.5 | 6 | 2000 | −1 | 10 | 12 | 6.5 |
| 13 | 0.5 | 8 | 2000 | −1 | 10 | 12 | 6.5 |
| 12 | 1.5 | 8 | 2000 | −1 | 10 | 12 | 19.5 |
| 2 | 0.5 | 6 | 10000 | −1 | 10 | 10 | 6.5 |
| 10 | 1.5 | 6 | 10000 | −1 | 10 | 10 | 19.5 |
| 14 | 0.5 | 8 | 10000 | −1 | 10 | 10 | 19.5 |
| 15 | 1.5 | 8 | 10000 | −1 | 10 | 10 | 6.5 |
| 11 | 0.5 | 6 | 2000 | 1 | 10 | 20 | 6.5 |
| 17 | 1.5 | 6 | 2000 | 1 | 10 | 20 | 19.5 |
| 26 | 0.5 | 8 | 2000 | 1 | 10 | 20 | 19.5 |
| 18 | 1.5 | 8 | 2000 | 1 | 10 | 20 | 6.5 |
| 22 | 0.5 | 6 | 10000 | 1 | 10 | 20 | 19.5 |
| 20 | 1.5 | 6 | 10000 | 1 | 10 | 20 | 6.5 |
| 21 | 0.5 | 8 | 10000 | 1 | 10 | 20 | 6.5 |
| 1 | 1.5 | 8 | 10000 | 1 | 10 | 20 | 19.5 |
| 8 | 1 | 7 | 6000 | 0 | 10 | 15 | 13 |
| 25 | 1 | 7 | 6000 | 0 | 10 | 15 | 13 |
| 24 | 0 | 7 | 6000 | 0 | 10 | 15 | 13 |
| 19 | 2 | 7 | 6000 | 0 | 10 | 15 | 13 |
| 3 | 1 | 5 | 6000 | 0 | 10 | 15 | 13 |
| 28 | 1 | 9 | 6000 | 0 | 10 | 15 | 13 |
| 9 | 1 | 7 | 2000 | 0 | 10 | 16 | 13 |
| 5 | 1 | 7 | 10000 | 0 | 10 | 15 | 13 |
| 4 | 1 | 7 | 6000 | −1 | 10 | 12 | 13 |
| 23 | 1 | 7 | 6000 | 1 | 10 | 18 | 13 |
| 6 | 1 | 7 | 6000 | 0 | 10 | 15 | 4 |
| 27 | 1 | 7 | 6000 | 0 | 10 | 15 | 30 |

TABLE C

Conditions for IL-18BP in PEG/(NH$_4$)$_2$SO$_4$

| Run Order | NaCl % [w/w] | pH | PEG Mw | Tie-line | (NH4)$_2$SO$_4$ % [w/w] | PEG % [w/w] | Temp [° C.] |
|---|---|---|---|---|---|---|---|
| 7 | 0.5 | 6 | 2000 | −1 | 12 | 12 | 19.5 |
| 16 | 1.5 | 6 | 2000 | −1 | 12 | 12 | 6.5 |
| 13 | 0.5 | 8 | 2000 | −1 | 12 | 12 | 6.5 |
| 12 | 1.5 | 8 | 2000 | −1 | 12 | 12 | 19.5 |
| 2 | 0.5 | 6 | 10000 | −1 | 12 | 12 | 6.5 |
| 10 | 1.5 | 6 | 10000 | −1 | 12 | 12 | 19.5 |
| 14 | 0.5 | 8 | 10000 | −1 | 12 | 12 | 19.5 |
| 15 | 1.5 | 8 | 10000 | −1 | 12 | 12 | 6.5 |
| 11 | 0.5 | 6 | 2000 | 1 | 20 | 20 | 6.5 |
| 17 | 1.5 | 6 | 2000 | 1 | 20 | 20 | 19.5 |
| 26 | 0.5 | 8 | 2000 | 1 | 20 | 20 | 19.5 |
| 18 | 1.5 | 8 | 2000 | 1 | 20 | 20 | 6.5 |
| 22 | 0.5 | 6 | 10000 | 1 | 20 | 20 | 19.5 |
| 20 | 1.5 | 6 | 10000 | 1 | 20 | 20 | 6.5 |
| 21 | 0.5 | 8 | 10000 | 1 | 20 | 20 | 6.5 |
| 1 | 1.5 | 8 | 10000 | 1 | 20 | 20 | 19.5 |
| 8 | 1 | 7 | 6000 | 0 | 16 | 16 | 13 |
| 25 | 1 | 7 | 6000 | 0 | 16 | 16 | 13 |
| 24 | 0 | 7 | 6000 | 0 | 16 | 16 | 13 |
| 19 | 2 | 7 | 6000 | 0 | 16 | 16 | 13 |
| 3 | 1 | 5 | 6000 | 0 | 16 | 16 | 13 |
| 28 | 1 | 9 | 6000 | 0 | 16 | 16 | 13 |
| 9 | 1 | 7 | 2000 | 0 | 16 | 16 | 13 |
| 5 | 1 | 7 | 10000 | 0 | 16 | 16 | 13 |
| 4 | 1 | 7 | 6000 | −1 | 12 | 12 | 13 |
| 23 | 1 | 7 | 6000 | 1 | 20 | 20 | 13 |
| 6 | 1 | 7 | 6000 | 0 | 16 | 16 | 4 |
| 27 | 1 | 7 | 6000 | 0 | 16 | 16 | 30 |

TABLE D

Conditions for IL-18BP in PEG/Na$_2$SO$_4$

| Run Order | NaCl % [w/w] | pH | PEG Mw | Tie-line | Na$_2$SO$_4$ % [w/w] | PEG % [w/w] | Temp [° C.] |
|---|---|---|---|---|---|---|---|
| 7 | 0.5 | 6 | 2000 | −1 | 10 | 10 | 19.5 |
| 16 | 1.5 | 6 | 2000 | −1 | 10 | 10 | 6.5 |
| 13 | 0.5 | 8 | 2000 | −1 | 10 | 10 | 6.5 |
| 12 | 1.5 | 8 | 2000 | −1 | 10 | 10 | 19.5 |
| 2 | 0.5 | 6 | 10000 | −1 | 10 | 10 | 6.5 |
| 10 | 1.5 | 6 | 10000 | −1 | 10 | 10 | 19.5 |
| 14 | 0.5 | 8 | 10000 | −1 | 10 | 10 | 19.5 |
| 15 | 1.5 | 8 | 10000 | −1 | 10 | 10 | 6.5 |
| 11 | 0.5 | 6 | 2000 | 1 | 15 | 15 | 6.5 |
| 17 | 1.5 | 6 | 2000 | 1 | 15 | 15 | 19.5 |
| 26 | 0.5 | 8 | 2000 | 1 | 15 | 15 | 19.5 |
| 18 | 1.5 | 8 | 2000 | 1 | 15 | 15 | 6.5 |
| 22 | 0.5 | 6 | 10000 | 1 | 15 | 15 | 19.5 |
| 20 | 1.5 | 6 | 10000 | 1 | 15 | 15 | 6.5 |
| 21 | 0.5 | 8 | 10000 | 1 | 15 | 15 | 6.5 |
| 1 | 1.5 | 8 | 10000 | 1 | 15 | 15 | 19.5 |
| 8 | 1 | 7 | 6000 | 0 | 12.5 | 12.5 | 13 |
| 25 | 1 | 7 | 6000 | 0 | 12.5 | 12.5 | 13 |
| 24 | 0 | 7 | 6000 | 0 | 12.5 | 12.5 | 13 |
| 19 | 2 | 7 | 6000 | 0 | 12.5 | 12.5 | 13 |
| 3 | 1 | 5 | 6000 | 0 | 12.5 | 12.5 | 13 |
| 28 | 1 | 9 | 6000 | 0 | 12.5 | 12.5 | 13 |
| 9 | 1 | 7 | 2000 | 0 | 12.5 | 12.5 | 13 |
| 5 | 1 | 7 | 10000 | 0 | 12.5 | 12.5 | 13 |
| 4 | 1 | 7 | 6000 | −1 | 10 | 10 | 13 |
| 23 | 1 | 7 | 6000 | 1 | 15 | 15 | 13 |
| 6 | 1 | 7 | 6000 | 0 | 12.5 | 12.5 | 4 |
| 27 | 1 | 7 | 6000 | 0 | 12.5 | 12.5 | 30 |

Due to the high number of samples generated during this first cycle (3 couples×28 experiments×2 phases=168), purified IL-18BP was used and protein concentration was estimated by UV absorbance at 280 nm. Experiments were performed at 2 ml-scale. The response collected was the partition coefficient K defined as:

$$K = \frac{C^{protein}_{top\_phase}}{C^{protein}_{bottom\_phase}} \quad \text{Equ 1}$$

Results

The raw data are described in Table E.

TABLE E

Results for the first cycle of factorial design experiments

| Run Order | PEG/KH$_2$PO$_4$ K$_{(IL-18BP)}$ | PEG/(NH$_4$)$_2$SO$_4$ K$_{(IL-18BP)}$ | PEG/Na$_2$SO$_4$ K$_{(IL-18BP)}$ |
|---|---|---|---|
| 7 | 1.5 | 99.7 | 12.3 |
| 16 | 0.3 | 41.1 | 7.3 |
| 13 | 2.0 | 289.8 | 5.9 |
| 12 | 0.6 | 67.4 | 3.1 |
| 2 | 1.8 | 6.1 | 12.7 |
| 10 | 0.5 | 8.4 | 8.7 |
| 14 | 2.9 | 26.7 | 5.8 |
| 15 | 2.4 | 49.0 | 7.2 |
| 11 | 0.7 | 97.2 | 22.0 |
| 17 | 0.5 | 65.9 | 37.1 |
| 26 | 2.3 | 113.1 | 25.7 |
| 18 | 1.7 | 170.4 | 11.5 |
| 22 | 1.1 | 324.5 | 101.6 |
| 20 | 0.8 | 132.8 | 21.9 |
| 21 | 4.7 | 78.4 | 59.8 |
| 1 | 2.3 | 132.9 | 32.5 |
| 8 | 1.3 | 65.3 | 60.3 |
| 25 | 1.6 | 3.2 | 58.9 |
| 24 | 4.0 | 9.0 | 49.7 |
| 19 | 0.5 | 64.0 | 36.5 |
| 3 | 1.1 | 72.4 | 45.4 |
| 28 | 5.7 | 145.1 | 129.7 |
| 9 | 0.6 | 253.7 | 19.7 |
| 5 | 2.1 | 129.0 | 43.6 |
| 4 | 0.8 | 23.1 | 8.5 |
| 23 | 1.6 | 131.2 | 135.5 |
| 6 | 1.2 | 48.1 | 48.7 |
| 27 | 0.5 | 196.3 | 94.3 |

The range of partition coefficient values collected for the three factorial design experiments are illustrated in Table F.

TABLE F

Range of partition coefficients values obtained after factorial design experiments using PEG/(NH$_4$)$_2$SO$_4$, PEG/KH$_2$PO$_4$ and PEG/Na$_2$SO$_4$ phase forming couples.

| | PEG/(NH$_4$)$_2$SO$_4$ | PEG/Na$_2$SO$_4$ | PEG/KH$_2$PO$_4$ |
|---|---|---|---|
| K$_{(IL18-BP)}$ | 9.9-73.0 | 4.4-163.2 | 0.2-3.0 |

A statistical analysis was performed on the partitioning of IL-18BP using PEG/Na$_2$SO$_4$ or PEG/KH$_2$PO$_4$. Factors with minor influence on protein partitioning were first eliminated of the statistical analysis. This analysis results in mathematical models (Equ 2 and Equ 3), predictive of the value of K, which takes into consideration the factors found to have significant effects on the response K.

Predictive Model of IL-18BP Partitioning Using PEG/Na$_2$SO$_4$ $$LnK(IL18\text{-}BP) = 4.11 + 0.26 \cdot PEGMw - 0.76 \cdot PEGMw^2 + 0.81 \cdot TL - 0.62 \cdot TL^2 \quad \text{Equ 2}$$

$R^2 = 0.81$, $SD = 0.49$

Predictive Model of IL-18BP Partitioning Using PEG/KH$_2$PO$_4$ $$LnK(IL18-BP) = 0.085 - 0.42 \cdot [NaCl] + 0.31 \cdot PEGMw + 0.47 \cdot pH + 0.18 \cdot pH^2 \quad \text{Equ 3}$$

$R^2 = 0.80$, $SD = 0.37$

Maximum K values from the predicted model are illustrated in Table G.

TABLE G

| | Maximum partition coefficient K predicted by the model | |
|---|---|---|
| | IL-18BP using PEG/Na$_2$SO$_4$ | IL-18BP using PEG/KH$_2$PO$_4$ |
| K | 81.5 | 3.4 |

Second Cycle of Factorial Design Experiments

The aim of this cycle of factorial design experiments was to select the appropriate conditions (pH, concentrations, etc.) showing extreme protein partitioning and good purification factors. This cycle was performed using PEG/Na$_2$SO$_4$ as phase forming components.

The experimental design was a central composite design. The design included a full two-level factorial, star points, and a centre point, with duplicates at each experimental setting. It resulted to 52 experiments, as shown in Table H.

TABLE H

Experimental conditions for the second cycle of factorial design experiments

| Run Order | PEG Mw | pH | NaCl % [w/w] | PEG % [w/w] | Na$_2$SO$_4$ % [w/w] |
|---|---|---|---|---|---|
| 1 | 6000 | 9 | 0 | 11.25 | 11.25 |
| 2 | 6000 | 5 | 0 | 13.75 | 13.75 |
| 3 | 6000 | 5 | 0 | 11.25 | 11.25 |
| 4 | 6000 | 9 | 0 | 11.25 | 11.25 |
| 5 | 6000 | 9 | 10 | 13.75 | 13.75 |
| 6 | 6000 | 5 | 10 | 11.25 | 11.25 |
| 7 | 6000 | 9 | 0 | 13.75 | 13.75 |
| 8 | 6000 | 5 | 0 | 11.25 | 11.25 |
| 9 | 6000 | 9 | 10 | 11.25 | 11.25 |
| 10 | 6000 | 7 | 5 | 12.50 | 12.50 |
| 11 | 6000 | 5 | 10 | 11.25 | 11.25 |
| 12 | 6000 | 7 | 5 | 12.50 | 12.50 |
| 13 | 6000 | 9 | 0 | 13.75 | 13.75 |
| 14 | 6000 | 5 | 10 | 13.75 | 13.75 |
| 15 | 6000 | 9 | 10 | 11.25 | 11.25 |
| 16 | 6000 | 5 | 0 | 13.75 | 13.75 |
| 17 | 6000 | 9 | 10 | 13.75 | 13.75 |
| 18 | 6000 | 5 | 10 | 13.75 | 13.75 |
| 19 | 8000 | 7 | 5 | 12.50 | 12.50 |
| 20 | 8000 | 7 | 5 | 12.50 | 12.50 |
| 21 | 8000 | 7 | 5 | 12.50 | 12.50 |
| 22 | 8000 | 7 | 0 | 12.50 | 12.50 |
| 23 | 8000 | 9 | 5 | 12.50 | 12.50 |
| 24 | 8000 | 7 | 5 | 10.00 | 10.00 |
| 25 | 8000 | 7 | 5 | 15.00 | 15.00 |
| 26 | 8000 | 5 | 5 | 12.50 | 12.50 |
| 27 | 8000 | 7 | 5 | 15.00 | 15.00 |
| 28 | 8000 | 7 | 10 | 12.50 | 12.50 |
| 29 | 8000 | 7 | 10 | 12.50 | 12.50 |
| 30 | 8000 | 7 | 5 | 12.50 | 12.50 |
| 31 | 8000 | 7 | 5 | 10.00 | 10.00 |
| 32 | 8000 | 9 | 5 | 12.50 | 12.50 |
| 33 | 8000 | 7 | 0 | 12.50 | 12.50 |
| 34 | 8000 | 5 | 5 | 12.50 | 12.50 |
| 35 | 10000 | 9 | 0 | 11.25 | 11.25 |
| 36 | 10000 | 5 | 0 | 13.75 | 13.75 |
| 37 | 10000 | 9 | 10 | 11.25 | 11.25 |
| 38 | 10000 | 5 | 0 | 11.25 | 11.25 |
| 39 | 10000 | 5 | 0 | 13.75 | 13.75 |
| 40 | 10000 | 7 | 5 | 12.50 | 12.50 |
| 41 | 10000 | 7 | 5 | 12.50 | 12.50 |
| 42 | 10000 | 9 | 0 | 13.75 | 13.75 |
| 43 | 10000 | 9 | 0 | 11.25 | 11.25 |
| 44 | 10000 | 5 | 10 | 11.25 | 11.25 |
| 45 | 10000 | 9 | 0 | 13.75 | 13.75 |
| 46 | 10000 | 9 | 10 | 13.75 | 13.75 |
| 47 | 10000 | 9 | 10 | 11.25 | 11.25 |
| 48 | 10000 | 5 | 10 | 11.25 | 11.25 |
| 49 | 10000 | 5 | 10 | 13.75 | 13.75 |
| 50 | 10000 | 5 | 10 | 13.75 | 13.75 |
| 51 | 10000 | 5 | 0 | 11.25 | 11.25 |
| 52 | 10000 | 9 | 10 | 13.75 | 13.75 |

Unlike the first cycle of factorial design experiments, clarified crude harvest was used as starting material. Experiments were performed at 10 ml-scale. Two responses were collected: the IL-18BP partition coefficient $K_{(IL-18BP)}$, related to the capacity of the process, and the total protein partition coefficient $K_{(tot\ prot)}$, related to the purification ability of the process.

Results

The raw data are presented in Table I.

TABLE I

Results for the second cycle of factorial design experiments

| | IL-18BP conc [mg/l] | | | total protein conc [mg/l] | | |
|---|---|---|---|---|---|---|
| Flask | Top phase | Bottom phase | $K_{(IL-18BP)}$ | Top phase | Bottom phase | $K_{(tot\ prot)}$ |
| 1 | 35.5 | 36.8 | 0.96 | 113 | 91 | 1.24 |
| 2 | 29.4 | 51.7 | 0.57 | 108 | 109 | 0.99 |
| 3 | 18.4 | 50 | 0.37 | 112 | 101 | 1.11 |
| 4 | 34.3 | 44 | 0.78 | 104 | 95 | 1.09 |
| 5 | 65.1 | 51.6 | 1.26 | 165 | 62 | 2.66 |
| 6 | 38.7 | 64.1 | 0.60 | 112 | 73 | 1.53 |
| 7 | 127 | 5.3 | 23.96 | 184 | 25 | 7.36 |
| 8 | 18.6 | 58.2 | 0.32 | 129 | 111 | 1.16 |
| 9 | 64.2 | 43.9 | 1.46 | 151 | 55 | 2.75 |
| 10 | 25.5 | 83.5 | 0.31 | 87 | 115 | 0.76 |
| 11 | 26.3 | 81.7 | 0.32 | 84 | 79 | 1.06 |
| 12 | 26.8 | 74.6 | 0.36 | 87 | 97 | 0.90 |
| 13 | 74.6 | 12.5 | 5.97 | 147 | 72 | 2.04 |
| 14 | 43.8 | 91.1 | 0.48 | 87 | 79 | 1.10 |
| 15 | 54.1 | 47.2 | 1.15 | 87 | 52 | 1.67 |
| 16 | 38.2 | 57.3 | 0.67 | 89 | 90 | 0.99 |
| 17 | 44.6 | 83.8 | 0.53 | 69 | 75 | 0.92 |
| 18 | 43.1 | 83 | 0.52 | 88 | 71 | 1.24 |
| 19 | 48.1 | 37.2 | 1.29 | 145 | 64 | 2.27 |
| 20 | 92.7 | 45 | 2.06 | 77 | 77 | 1.00 |
| 21 | 51.5 | 45.5 | 1.13 | 108 | 66 | 1.64 |
| 22 | 34.6 | 44.8 | 0.77 | 102 | 89 | 1.15 |
| 23 | 87.1 | 36.3 | 2.40 | 147 | 82 | 1.79 |
| 24 | 26.1 | 64.1 | 0.41 | 95 | 91 | 1.04 |
| 25 | 25.5 | 5.3 | 4.81 | 106 | 56 | 1.89 |
| 26 | 61.4 | 45.2 | 1.36 | 147 | 77 | 1.91 |
| 27 | 64.1 | 2.65 | 24.19 | 114 | 53 | 2.15 |
| 28 | 110 | 33 | 3.33 | 195 | 48 | 4.06 |
| 29 | 49.5 | 45 | 1.10 | 153 | 64 | 2.39 |
| 30 | 34.8 | 51.7 | 0.67 | 138 | 99 | 1.39 |
| 31 | 26.2 | 60.4 | 0.43 | 103 | 95 | 1.08 |
| 32 | 37.5 | 39.3 | 0.95 | 106 | 79 | 1.34 |
| 33 | 37.7 | 53.2 | 0.71 | 112 | 83 | 1.35 |
| 34 | 31.1 | 38.9 | 0.80 | 106 | 82 | 1.29 |
| 35 | 33.6 | 34.6 | 0.97 | 107 | 87 | 1.23 |

TABLE I-continued

Results for the second cycle of factorial design experiments

| | IL-18BP conc [mg/l] | | | total protein conc [mg/l] | | |
|---|---|---|---|---|---|---|
| Flask | Top phase | Bottom phase | $K_{(IL-18BP)}$ | Top phase | Bottom phase | $K_{(tot\ prot)}$ |
| 36 | 29.4 | 27.7 | 1.06 | 184 | 93 | 1.98 |
| 37 | 47 | 32.1 | 1.46 | 161 | 55 | 2.93 |
| 38 | 13.3 | 44.5 | 0.30 | 102 | 94 | 1.09 |
| 39 | 36.6 | 23.1 | 1.58 | 138 | 74 | 1.86 |
| 40 | 27.7 | 47.4 | 0.58 | 125 | 82 | 1.52 |
| 41 | 29.8 | 46.8 | 0.64 | 108 | 86 | 1.26 |
| 42 | 79.2 | 8.9 | 8.90 | 353 | 70 | 5.04 |
| 43 | 23.8 | 41.7 | 0.57 | 118 | 117 | 1.01 |
| 44 | 42 | 42.1 | 1.00 | 143 | 67 | 2.13 |
| 45 | 62.8 | 8.02 | 7.83 | 191 | 78 | 2.45 |
| 46 | 110 | 11.1 | 9.91 | 354 | 37 | 9.57 |
| 47 | 61.1 | 28.8 | 2.12 | 217 | 56 | 3.88 |
| 48 | 38.4 | 41.6 | 0.92 | 154 | 65 | 2.37 |
| 49 | 61.1 | 23.3 | 2.62 | 174 | 51 | 3.41 |
| 50 | 86.5 | 17.4 | 4.97 | 271 | 50 | 5.42 |
| 51 | 14 | 47.1 | 0.30 | 103 | 130 | 0.79 |
| 52 | 70.8 | 16 | 4.43 | 212 | 65 | 3.26 |

The ranges of partition coefficient values observed for the factorial design experiments are illustrated in Table J.

TABLE J

Range of partition coefficients values for IL-18BP and total proteins obtained by factorial design experiments using PEG/Na2SO4

| $K_{(IL-18BP)}$ | $K_{(tot.\ prot.)}$ |
|---|---|
| 0.3-24.2 | 0.8-9.6 |

A statistical analysis was performed on the partitioning of IL-18BP and of total proteins. In contrast to the first cycle of experiments, the results of this analysis reported in Table K and Table L indicate that all four main factors tested were found significant, as were many second-degree interactions.

TABLE K

Output from the quadratic regression model for $lnK_{(IL-18BP)}$

| Factor | Value | Std. Err |
|---|---|---|
| Intercept | −0.0552 | 0.1652 |
| [NaCl] | 0.0854 | 0.0886 |
| pH | 0.5462 | 0.0886 |
| PEG Mw | 0.3254 | 0.0886 |
| Tie.line | 0.6627 | 0.0767 |
| $[NaCl]^2$ | 0.3325 | 0.2254 |
| $PH^2$ | 0.3861 | 0.2254 |
| $(PEG\ Mw)^2$ | −0.6413 | 0.2254 |
| $(Tie-line)^2$ | 0.2092 | 0.074 |
| [NaCl]*pH | −0.2428 | 0.0939 |
| [NaCl]*PEG Mw | 0.3163 | 0.0939 |
| [NaCl]*Tie.line | −0.2988 | 0.0939 |
| pH*PEG Mw | −0.0921 | 0.0939 |
| pH*Tie-line | 0.1501 | 0.0939 |
| PEG Mw*Tie-line | 0.2287 | 0.0939 |

Residual standard error: 0.5314 on 37 degrees of freedom; Multiple R-Squared: 0.8312; F-statistic: 13.01 on 14 and 37 degrees of freedom, the p-value is 2.763e−010

TABLE L

Output from the quadratic regression model for $lnK_{(tot\ prot.)}$

| Factor | Value | Std. Err |
|---|---|---|
| Intercept | 0.2798 | 0.115 |
| [NaCl] | 0.2314 | 0.0586 |
| pH | 0.2023 | 0.0586 |
| PEG Mw | 0.246 | 0.0586 |
| Tie.line | 0.2072 | 0.0508 |
| $NaCl^2$ | 0.3959 | 0.1496 |
| $PH^2$ | 0.1639 | 0.1496 |
| $(PEG\ Mw)^2$ | −0.216 | 0.1496 |
| $(Tie-line)^2$ | 0.0254 | 0.0496 |
| [NaCl]*pH | −0.044 | 0.0622 |
| [NaCl]*PEG Mw | 0.2048 | 0.0622 |
| [NaCl]*Tie.line | −0.1369 | 0.0622 |
| pH*PEG Mw | −0.0468 | 0.0622 |
| pH*Tie-line | 0.087 | 0.0622 |
| PEG Mw*Tie-line | 0.1482 | 0.0622 |

Residual standard error: 0.3517 on 36 degrees of freedom; Multiple R-Squared: 0.7351; F-statistic: 7.138 on 14 and 36 degrees of freedom, the p-value is 9.826e−007

The predictive models of the second cycle of factorial design experiments allowed the selection of 28 candidate conditions, which show a predicted yield >75% and a purity in post-A2PS fraction higher than 50%. These are considered as "leads" for further development. The candidate conditions are listed in Table M.

TABLE M

Candidate conditions selected from a statistical analysis of the second cycle of factorial design experiments

| Conditions | NaCl % [w/w] | pH | PEG Mw | PEG % [w/w] | $Na_2SO_4$ % [w/w] |
|---|---|---|---|---|---|
| val2-1 | 0 | 5 | 10000 | 10 | 10 |
| val2-2 | 0 | 7 | 10000 | 10 | 10 |
| val2-3 | 10 | 5 | 6000 | 10 | 10 |
| val2-4 | 10 | 7 | 10000 | 10 | 10 |
| val2-5 | 0 | 5 | 10000 | 11.25 | 11.25 |
| val2-6 | 0 | 7 | 10000 | 11.25 | 11.25 |
| val2-7 | 10 | 9 | 6000 | 12.5 | 12.5 |
| val2-8 | 0 | 5 | 6000 | 10 | 10 |
| val2-9 | 0 | 9 | 8000 | 13.75 | 13.75 |
| val2-10 | 0 | 7 | 6000 | 15 | 15 |
| val2-11 | 0 | 9 | 6000 | 15 | 15 |
| val2-12 | 5 | 9 | 6000 | 15 | 15 |
| val2-13 | 0 | 5 | 8000 | 15 | 15 |
| val2-14 | 5 | 5 | 8000 | 15 | 15 |
| val2-15 | 0 | 7 | 8000 | 15 | 15 |
| val2-16 | 5 | 7 | 8000 | 15 | 15 |
| val2-17 | 0 | 9 | 8000 | 15 | 15 |
| val2-18 | 5 | 9 | 8000 | 15 | 15 |
| val2-19 | 10 | 9 | 8000 | 15 | 15 |
| val2-20 | 0 | 5 | 10000 | 15 | 15 |
| val2-21 | 0 | 7 | 10000 | 15 | 15 |
| val2-22 | 5 | 7 | 10000 | 15 | 15 |
| val2-23 | 0 | 9 | 10000 | 15 | 15 |
| val2-24 | 5 | 9 | 10000 | 15 | 15 |
| val2-25 | 10 | 9 | 10000 | 15 | 15 |
| val2-26 | 10 | 7 | 8000 | 10 | 10 |
| val2-27 | 10 | 5 | 6000 | 12.5 | 12.5 |
| val2-28 | 10 | 7 | 6000 | 12.5 | 12.5 |

Experimental Verification of the Leads Predicted by the Predictive Model

The aim of these experiments was to verify experimentally the performance of the leads predicted by the statistical analysis. Clarified crude harvest was used as starting material. Experiments were performed at 10 ml-scale. Two responses were collected: the IL-18BP partition coefficient $K_{(IL-18BP)}$, and the total protein partition coefficient $K_{(tot\ prot)}$. Experimental conditions are described in Table M above.

Results

Results are reported in Table N. The concentration of IL-18BP was measured by BIAcore with an immobilized monoclonal antibody detecting IL-18BP, designated Mab 582.1. IL-18BP concentration was measured by Biacore® method according to the manufacturer's protocol, using the following parameters:

| Bulk characterisation | Units | Specification | BULK 1 7075-035-01 UF2 | BULK 2 7075-41-05 UF2 |
|---|---|---|---|---|
| Quantitation | | | | |
| Protein content | mg/mL; alpha = 1.26 at 280 nm | | 0.584 | 0.171 |
| RP-HPLC | mg/mL | | 0.586 | 0.141 |
| Product conformity | | | | |
| Isoform profile by IEF/WB | | cluster of bands falls below pI4.6 as in reference | atypique (cluster below pI 3.5) | atypique (cluster below pI 4.2) |
| Isoform profile by CZE | % | M0 + M1 < 30% | M0 = 0% M1 = 13.7% | M0 = 0.6% M1 = 10.3% |
| | % | M2 | M2 = 68.6% | M2 = 71.6% |
| | % | M3 | M3 = 17.7% | M3 = 17.5% |
| Product based impurities | | | | |
| Dimers and higher molecular weight (SE-HPLC) | % | | 92.6 | 93.3 |
| Dimers and higher molecular weight (SDS/WB) | % | | Dimers: 8%(28%) Aggregats: 0%(15%) | Dimers: 0%(33%) Aggregats: 0%(n/a) |
| Truncated forms (SDS/WB) | % | | 21% (22%) | 4% (7%) |
| Process based impurities | | | | |
| Cell culture derived protein contaminations (Immunoassay) | ng/mg | | 51 | 69 |
| Residual DNA | | | not performed | not performed |

TABLE N

Experimental results from the canditate conditions

| Conditions | Balance IL-18BP | Yield % | Purity % (Biacore/Bradford) |
|---|---|---|---|
| Harvest | B76.B1377.237 | | 40 |
| val2-1 | 1.07 | 107 | 69 |
| val2-2 | 1.12 | 112 | 56 |
| val2-3 | 1.19 | 65 | 93 |
| val2-4 | 1.08 | 86 | 59 |
| val2-5 | 0.99 | 98 | 92 |
| val2-6 | 0.91 | 89 | 59 |
| val2-7 | 1.16 | 64 | 66 |
| val2-8 | 0.89 | 54 | 32 |
| val2-9 | 0.62 | 54 | 55 |
| val2-10 | 0.18 | 11 | 19 |
| val2-11 | 0.13 | 11 | 31 |
| val2-12 | 0.35 | 30 | 43 |
| val2-13 | 0.10 | 6 | 20 |
| val2-14 | 0.21 | 19 | 32 |
| val2-15 | 0.59 | 54 | 42 |
| val2-16 | 0.91 | 67 | 65 |
| val2-17 | 0.11 | 8 | 29 |
| val2-18 | 1.01 | 74 | 74 |
| val2-19 | 1.01 | 60 | 63 |
| val2-20 | 0.10 | 7 | 36 |
| val2-21 | 0.06 | 4 | 18 |
| val2-22 | 0.34 | 20 | 56 |
| val2-23 | 0.10 | 4 | 11 |
| val2-24 | 0.72 | 52 | 36 |
| val2-25 | 1.00 | 54 | 0 |
| val2-26 | 1.13 | 75 | 77 |
| val2-27 | 1.00 | 64 | 97 |
| val2-28 | 1.04 | 56 | 89 |

Three leads have been identified from the statistical model. Parameters relating to these leads are illustrated in Table O below. The Capillary Zone Electrophoresis (CZE) was carried out according to the following protocol:

Materials and Equipment for Capillary Zone Electrophoresis

| Materials | |
|---|---|
| MilliQ purified water | Millipore or equivalent |
| Trifluoroacetic acid (TFA) cod. 9470 | Baker or equivalent |
| Acetonitrile (CH$_3$CN) (Cat. no. 30) | Merck or equivalent |
| NaOH 50% "Baker analyzed" Cat. no. 7067 | Baker |
| eCAP ™ Phosphate buffer 50 mM, pH 7.0 (Cat. no. 477423) | Beckman Coulter |
| Interim Reference Material ST1P01/r-hIL-18BP | Serono |
| Neutral marker (Cat. no. 477434) | Beckman Coulter |

Equipments

| | |
|---|---|
| P/ACE MDQ System | Beckman Coulter |
| 32 Karat ™ software version 4.0 | Beckman Coulter |
| eCAP ™ Capillary tubing 75 µm I.D. (Cat. no. 338454) | Beckman Coulter |
| PCR Vials (Cat. no. 144709) | Beckman Coulter |
| Micro Vial Springs (Cat. no. 358821) | Beckman Coulter |
| PCR Vials Caps (Cat. no. 144656) | Beckman Coulter |
| Vial Holders (Cat. no. 144657) | Beckman Coulter |
| P/ACE System MDQ cartridge (Cat. no 144738) | Beckman Coulter |
| Sep-Pak Plus tC2 Cartridge (Cat. No. WAT052720) | Waters |
| Centricon YM-10 (Cat. No. 4206) Millipore | Millipore |
| Millipore or equivalent | |
| 1 mL and 5 mL syringes | |

Solutions for Sep-Pak
Sep-Pak conditioning: 100% CH$_3$CN
Sep-Pak equilibrating/washing solution: 25% CH$_3$CN in 0.1% aqueous TFA
Sep-Pak eluting solution: 36% CH$_3$CN in 0.1% aqueous TFA (expiration: two weeks at 4° C.)
Solutions for CZE
5 mM phosphate CZE wash/run buffer
Prepare by 1:10 dilution of 50 mM phosphate stock solution pH 7.0. Filter through 0.22 µm filter. Prepare fresh.
0.5 M NaOH (CZE washing solution)
Add 26.2 µL 50% NaOH to water, 1 mL total volume. Prepare fresh.
1M NaOH (CZE regeneration solution)
Add 52.4 µL 50% NaOH to water, 1 mL total volume. Prepare fresh.
Neutral Marker (dilution 1:10000)
Add 10 µL neutral marker stock solution to water, 1 mL total volume.
Add 10 µL of this neutral marker 1:100 dilution to water, 1 mL total volume.
Store for three months at 4° C.

Method
CZE is a form of high-performance capillary electrophoresis. The capillary is filled with electrolyte buffer and sample separation occurs by applying an electric field across the capillary. The separation mechanism is based on differences in electrophoretic mobility between analyses. Electrophoretic mobility is a function of each analyte's net charge and hydrodynamic size at a given condition.
CZE analysis of samples containing IL-18BP is performed using a CE system with a fused-silica capillary (75 µm ID and effective length of 50 cm) filled with a buffer containing 5 mM phosphate.

To increase CZE resolution, the standard Reference and each bulk is desalted by Centricon 10 before CZE analysis. Samples are loaded at about 2.5 mg/mL IL-18BP concentration. Injection into the capillary is performed using a low-pressure injection (≈0.5 psi) for 5 seconds. The separation is performed at a constant voltage of 25 KV for 30 min at 25° C. The run is monitored using UV absorbance at 214 nm.

For the Reference Standard and bulk samples the procedure consists in two steps: sample desalting and CZE analysis.

For crude harvest and post-capture samples the high matrix interference is removed to allow observing the IL-18BP glycoprotein profile. In this case, the procedure consists of three steps: a Sep-Pak capture step to remove the high matrix interference, sample desalting, and CZE analysis of captured IL-18BP fraction.

IL-18BP Capture by Sep-Pak Procedure for CZE Analysis of Crude Harvest and Post-capture Samples
Assemble the Sep-Pak cartridge with a 5 mL syringe, then follow the procedure below:

TABLE (ii)

| Step | Solution | Volume | Eluate |
|---|---|---|---|
| Conditioning (1) | 100% CH$_3$CN | 5 mL | discard |
| Equilibration (2) | 25% CH$_3$CN in 0.1% aqueous TFA | 5 mL | discard |
| Sample loading (3) * | | 0.5 mL | discard |
| Washing (4) | 25% CH$_3$CN in 0.1% aqueous TFA | 5 mL | discard |
| Elution (5) | 36% CH$_3$CN in 0.1% aqueous TFA | 0.6 mL | discard |
| Elution (6) | 36% CH$_3$CN in 0.1% aqueous TFA | 2.0 mL | Collect ** |

* Load up to 500 µL of sample having IL-18BP concentration ≧250 µg/mL. If IL-18BP sample concentration is 70 ÷ 250 µg/mL a higher volume is needed, in this case load any additional up to 500 µL sample after 2 mL equilibrating buffer. For diluted samples, concentrate to 500 µL by Centricon/Centriplus 10 ultrafiltration at 10° C. temperature.
** Collect the eluate in a vial containing 1 mL 50 mM Phosphate buffer pH 7.0

The collected solution from step 6 (total volume 3 mL) is concentrated in a Speed-Vac centrifuge to eliminate CH$_3$CN and reduce total volume to ≦2.0 mL.

Sample Desalting by Centricon 10 Ultrafiltration
The Reference Standard, or the bulk or the Speed-Vac solution resulting from the previous step is transferred in Centricon 10 and concentrated to about 100 µL by ultrafiltration at 5000×g and 10° C.

Desalting is then performed with four 1 mL H$_2$O washing at 5000×g and 10° C. temperature, for 40 minutes each.

Except crude harvest, retentates are diluted and aliquoted (30 µL aliquots) at 2.5 mg/mL IL18-BP concentration.

Crude harvest samples are recovered in 40-50 µL final volume. This amount is sufficient to prepare two independent CZE samples. The samples are now ready for CZE analysis.

Store all the samples at −20° C. up to CZE analysis.

CZE Analysis
Transfer ≧20 µL sample/reference in PCR vials containing 1/10 volume of neutral marker (3.3.4), mix by reverse pupating and avoid generating bubbles.

Recommended Electrophoretic Parameters:
Add the following reagents into separate vial holders and avoid generating bubbles.

TABLE (iii)

| Inlet reagents | Reagent volume | Outlet reagents | Reagent volume |
|---|---|---|---|
| Wash buffer (3.3.1) | 1.2 mL | | |
| Run Buffer (3.3.1) | 1.2 mL | Run Buffer (3.3.1) | 1.2 mL |
| Purified water | 1.2 mL | Purified water | 1.2 mL |
| CZE washing solution (3.3.2) | 1.0 mL | | |
| CZE regenerating solution (3.3.3) * | 1.0 mL | | |
| Sample | >22 μL/PCR Vial | | |
| | | Waste (purified water) 1 | 0.2 mL |
| | | Waste (purified water) 2 | 0.2 mL |
| Air * | | Empty Vial | |

* use only if required

CZE Analysis Time Table

TABLE (iii)

| Event | Value | Duration | Inlet Vial | Volume reagent | Outlet Vial |
|---|---|---|---|---|---|
| Rinse pressure | 20.0 psi | 2.00 min | Wash buffer (3.3.1) | 1.2 mL | Waste 1 (0.2 mL) |
| Inject-pressure | 0.5 psi | 5.0 sec | Sample | ≧22 μL | Run Buffer (3.3.1) |
| Separate-Voltage | 25 KV | 30.00 min | Run Buffer (3.3.1) | 1.2 mL | Run Buffer (3.3.1) |
| Rinse pressure | 20.0 psi | 1.00 min | Wash buffer (3.3.1) | 1.2 mL | Waste 1 (0.2 mL) |
| Rinse pressure | 20.0 psi | 1.00 min | Purified water | 1.2 mL | Waste 1 (0.2 mL) |
| Rinse pressure | 20.0 psi | 1.00 min | CZE washing solution (3.3.2) | 1.0 mL | Waste 2 (0.2 mL) |
| Rinse pressure | 40.0 psi | 2.00 min | Purified water | 1.2 mL | Waste 2 (0.2 mL) |
| Rinse pressure | 40.0 psi | 2.00 min | Wash buffer (3.3.1) | 1.2 mL | Waste 2 (0.2 mL) |
| Wait | | | Wash buffer (3.3.1) | 1.2 mL | Run Buffer (3.3.1) |

CZE Capillary Regeneration Time Table

TABLE (iv)

| Event | Value | Duration | Inlet Vial | Volume reagent | Outlet Vial |
|---|---|---|---|---|---|
| Rinse pressure | 40.0 psi | 1.00 min | Purified water | 1.2 mL | Waste 2 (0.2 mL) |
| Rinse pressure | 40.0 psi | 10.00 min | CZE regenerating solution (3.3.3) | 1.0 mL | Waste 2 (0.2 mL) |
| Rinse pressure | 40.0 psi | 4.00 min | Purified water | 1.2 mL | Waste 2 (0.2 mL) |
| Rinse pressure | 40.0 psi | 1.00 min | Wash buffer (3.3.1) | 1.2 mL | Waste 2 (0.2 mL) |
| Rinse pressure | 0.5 psi | 30.00 min | Wash buffer (3.3.1) | 1.2 mL | Waste 2 (0.2 mL) |
| Wait | | | Run Buffer (3.3.1) | 1.2 mL | Run Buffer (3.3.1) |

| | |
|---|---|
| Capillary length to detector/total length | 50/60 cm |
| Polarity | positive to negative (forward) |
| Temperature | capillary = 25 ± 2 C.° |
| sample tray = | 10 ± 2 C.° |
| Detection | 214 nm |

Recommended Injection Protocols

At least three injections of the Standard Reference material for the purpose of capillary conditioning.
Standard Reference 1 (start)
Single injection of sample 1
Single injection of sample 2
Single injection of sample 3
Single injection of sample 4
Standard Reference 2 (end)

NOTE: To increase reproducibility, a maximum of 4 samples can be analyzed in one sequence between reference 1 and reference 2 by using the same CZE running buffer. Alternatively two bracketing references can be used for each sample as described below.

At least three injections of the Standard Reference material are done for the purpose of capillary conditioning.
Standard Reference (start 1)
Single injection of sample 1
Standard Reference (end1/start2)
Single injection of sample 2
Standard Reference replicate (end2/start3)
Single injection of sample 3
Standard Reference replicate (end3)

Data Analysis

The Standard Reference material is used for comparison of sample data.

Print the overlaid and stacked electroferograms of sample/s and both bracketing Reference standard (start/end) and archive them in the file results.

Determination of Migration Times MT2 and MT3

Determine the migration times MT2 and MT3 at the left and right valleys of −3 and +3 peaks of the Reference Standard (Start). The 0 peak is the principal peak of the reference.

Isoforms Classification

Due the high acidity of IL-18BP glycoprotein profile, the isoforms between MT2 and MT3 are named "acidic isoforms" Isoforms with migration times higher then MT3 are named "highly acidic isoforms" Isoforms with migration times lower then MT2 are named "less acidic isoforms".

In some circumstances, it might be necessary to add the class of "basic isoforms" defined as isoforms with migration times lower then MT1.

Isoforms Abundance Estimation

Analyze the reference and each sample by using the functions: manual peak between MT1-M2, MT2-MT3 and MT3-MT4; the manual baseline between 5 and 28 minutes and integration OFF between 0 and MT1 and between MT4 and 30 minutes. Manually modify the functions Width and Threshold to obtain an integration of three groups of peaks between MT1-M2 (less acidic isoforms), MT2-MT3 (acidic isoforms) and MT3-MT4 (highly acidic isoforms) similar to that showed above for the Reference Standard.

$$\% \text{ isoform abundance} = \frac{\text{area}\begin{pmatrix} MT1-MT2 \text{ or} \\ MT2-MT3 \text{ or} \\ MT3-MT4 \end{pmatrix}}{\text{Total area } (MT1-MT4)}$$

When necessary, add the group of peaks corresponding to "basic isoforms" defined as isoforms with migration times lower then MT1, and accordingly correct the above formula.

Results of the CZE Analysis

The CZE profiles showed that acidic isoforms seemed to be selected by A2PS. The results of the is from profiles are depicted in FIG. 1.

Calculation of Yield and Purity

The yield and purity of the purified IL-18BP were calculated as follows:

Yield:

$$Y = \frac{V_{phase} \cdot C_{phase}^{IL18BP}}{V_0 \cdot C_0^{IL18BP}} \cdot 100$$

Purity:

$$\text{purity} = \frac{C_{phase}^{IL18BP}}{C_{phase}^{tot\_prot.}} \cdot 100$$

$V_{phase}$: volume of the phase of interest
$C_{phase}^{IL18BP}$: Concentration of IL18BP in the phase of interest
$C_{phase}^{tot\_prot}$: Concentration of total protein in the phase of interest
$V_0$: volume of the starting material to be purified
$C_0^{IL18BP}$: Concentration of IL18BP in the starting material to be purified.

Results

The parameters measured for the three leads are summarized in Table O. Protein partitioning was reproducible (see standard deviation values). No aggregates were formed during the process.

TABLE O

Experimental performance of the leads selected from the statistical model for direct capture of IL-18BP using aqueous two-phase system.

| Label | Mass balance IL-18BP | Yield [%] | Purity* [%] (IL-18BP/ total proteins) | Aggregates [%] (SDS-PAGE/WB) |
|---|---|---|---|---|
| Starting material: B76.B1377.237 | | | 40 | 23 |
| Val2-1 (n = 3) | 1.1 ± 0.07 | 107 ± 5 | 69 ± 5 | 22 |
| Val2-2 (n = 4) | 1.1 ± 0.10 | 112 ± 7 | 56 ± 6 | 22 |
| Val2-5 (n = 4) | 1.0 ± 0.05 | 98 ± 3 | 92 ± 4 | 21 |

*IL-18BP assay with Biacore, total protein assay with the Bradford method

A2PS Process Using Unqualified Harvest.

In this section, the direct purification of IL-18BP from crude unqualified harvest was assessed. In order to compare if cells affect the process performance, two process conditions have been compared with and without cells (for process conditions, see Table N.

As shown in Table P, process performances were relatively little affected by the presence of cells or cell debris. After phase separation, most of the cells and cell debris were located at a thick interphase.

TABLE P

Comparison of process performance using clarified crude harvest and unclarified crude harvest

| Conditions | $K_{(IL-18BP)}$ | $K_{(tot\ prot)}$ |
|---|---|---|
| val2-17 clarified | 8.4 | 2.7 |
| val2-17 unclarified | 13.1 | 2.6 |
| val2-21 clarified | 4.6 | 1.7 |
| val2-21 unclarified | 5.1 | 2.2 |
| val2-23 clarified | 2.5 | 0.9 |
| val2-23 unclarified | 1.8 | 1.2 |
| val2-25 clarified | 1.3 | 2.9 |
| val2-25 unclarified | 1.0 | 3.3 |

Optimization of the Leads

The aim of these experiments was to optimize the performance of the leads selected previously (Table O). It is possible to optimize the yield, the purity or the concentration factor of the extraction step based on the tie-lines.

Na$_2$SO$_4$ Concentration

Conductimetry is commonly used for the determination of salt concentration in A2PS. However, culture media already contain some salt that can affect the analysis. Therefore, a colorimetric assay (Kit: Aquanal-plus Sulfate (SO$_4$)50-330 mg/l (Fluka° 37429-1EA) was used and show better results in that case.

PEG Concentration

Refractometry can be used for PEG concentration analysis. However, many culture media components interfere with the analysis. Therefore, size exclusion chromatography was used for PEG concentration analysis under the conditions reported in Table Q.

TABLE Q

Conditions for size exclusion chromatography

| Detection | RI |
|---|---|
| Temperature | 40° C. |
| Column | Shodex SB-804 |
| Pressure | 30 bars |
| Flux | 0.8 ml/min |
| Eluent | $H_2O$ |
| Injection volume | 20 µl |
| Retention time | 26 min. |

Figure 5:
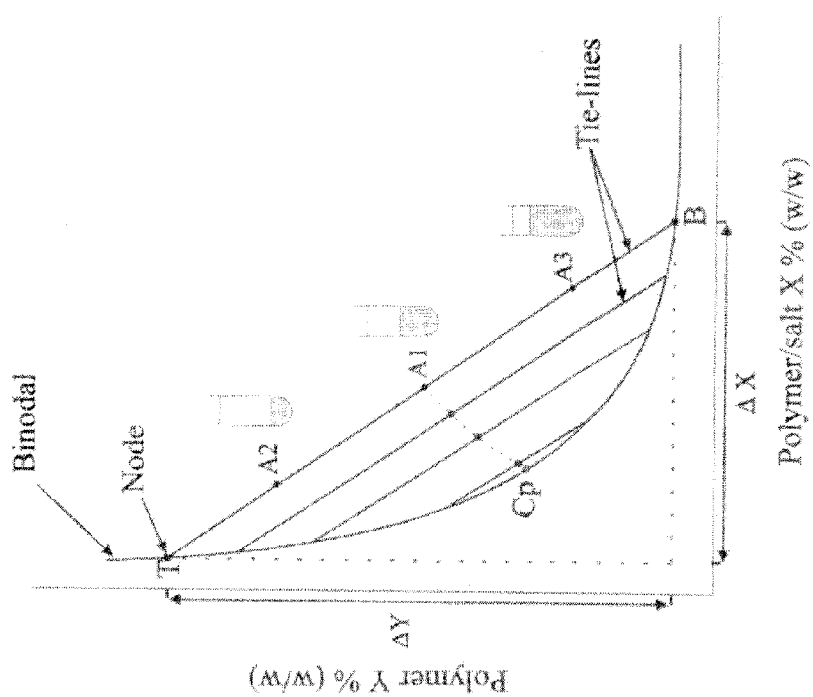
FIG. 5 illustrates the principle of establishing a tie-line in an aqueous two-phase system (taken from Hatti-Kaul, 2000).

Tie-lines can be determined by measuring the PEG and $Na_2SO_4$ in the top and bottom phases (see FIGS. 4, 5 and 6). $K_{(IL-18BP)}$ and $K_{(tot\ prot)}$ are constant on the same tie-line. Hence, an optimal phase ratio chosen for the purification process would provide a balance between yield and purification factor.

Clarified crude harvest was used as starting material and the experiments were performed at 10 ml-scale. Two responses were collected: the IL-18BP partition coefficient $K_{(IL-18BP)}$, and the total protein partition coefficient $K_{(tot\ prot)}$.

Results

Four optimized experimental conditions have been tested. Table R summarizes the experimental process performance obtained after partitioning.

TABLE R

Optimized process conditions based on tie-lines calculation

| Conditions | NaCl % [w/w] | pH | PEG Mw | PEG % [w/w] | $Na_2SO_4$ % [w/w] |
|---|---|---|---|---|---|
| val2-1 opt1 | 0 | 5 | 10000 | 28.6 | 1.9 |
| val2-2 opt1 | 0 | 7 | 10000 | 28.75 | 2.25 |
| val2-2 opt2 | 0 | 7 | 10000 | 21 | 5.5 |
| val2-5 opt1 | 0 | 5 | 10000 | 27.9 | 2.8 |

Depending on the downstream process and the quality of the final bulk, many more optimized conditions may be selected based on the tie-lines that are shown in FIGS. 2, 3 and 4. The flexibility regarding yield, the purity or the concentration factor based on the tie-lines is one of the major advantages of A2PS technology.

TABLE S

Process performance after optimization of the conditions val2-1, val2-2, val2-5.

| Label | Mass balance IL-18BP | Yield [%] Exp | Concentration factor Exp | Purity* [%] (IL-18BP/total proteins) Exp |
|---|---|---|---|---|
| Starting material: B76 0007-E | | | | 47 |
| Val2-1 opt1 | 0.96 | 93 | 14.7 | 65 |
| Val2-2 opt1 | 1.04 | 99 | 13.3 | 62 |
| Val2-2 opt2 | 0.98 | 98 | 2.3 | 81 |
| Val2-5 opt1 | 0.88 | 88 | 6.6 | 88 |

*IL-18BP assay with Biacore, total protein assay with the Bradford method

IL-18BP Direct Capture at 1-liter Scale.

The aim of these experiments was to evaluate the major scale-up issues related to A2PS technology. Two conditions from Table R and Table S have been selected for a 100-fold scale up (val2-5; val2-2 opt2). Results are illustrated in Table T. No large differences in process performance can be observed after a 100-fold scale-up.

TABLE T

Comparison of process performances at 10 ml-scale and 1000 ml-scale for the conditions val2-5 and val2-2 opt2.

| Label | Mass balance IL18BP | Yield | Purity Biacore/bradford | Purif. fact. | Conc. fact. | Aggregates | CZE Basic | Less acid | Acid | Highly acid |
|---|---|---|---|---|---|---|---|---|---|---|
| Harvest B76 0007-E | | | 40% | | | 21% | 5.3 | 24.3 | 53.8 | 16.1 |
| Val2-5 10 ml | 0.99 | 98 | 92% | 2.32 | 1.4 | 21% | 2% | 23.9% | 56.4% | 17.8% |
| Val2-5 1000 ml | 1.12 | 110 | 86% | 2.15 | 1.5 | 21% | 2.5% | 24.1% | 49.1% | 24.3% |
| Val2-2 opt2 10 ml | 0.96 | 93 | 65% | 1.27 | 14.7 | 23% | 2.8% | 21.3% | 55.1% | 20.8% |
| Val2-2 opt2 1000 ml | 1.06 | 101 | 62% | 1.27 | 11.6 | 27% | 3.9% | 19.0% | 57.7% | 19.5% |

Effect of A2PS Process on Protein Integrity and Bulk Quality

In order to estimate if direct capture of IL-18BP using A2PS technology affects final bulk quality, post-A2PS-capture material from the scale-up experiment val-2.5 has been purified using further chromatographic purification steps. Results are illustrated in Table U. In comparison with a lot of drug substance obtained with a chromatographic capture on Fractogel® TMAE (trimethylaminoethyl ion exchange chromatography, purchased from Merck), the lot (7075-41-05 UF2) derived from the A2PS capture shows comparable quality results.

REFERENCES

1. Ageland, H., Nystrom, L., Person, J., and Tjemeld, F. Process for purifying a protein. (U.S. Pat. No. 6,559,284). 2003. Esperion Therapeutics, Inc. (Ann Arbor, Mich.).
2. Altschul S F et al, J Mol Biol, 215, 403-410, 1990
3. Altschul S F et al, Nucleic Acids Res., 25:389-3402, 1997
4. Ananthapadmanabhan, K. P. and Goddard, E. D. (U.S. Pat. No. 4,743,550). 1988. (to Union Carbide Corporation).
5. Balasubramaniam, D., Wilkinson, C., van Cott, K., & Zhang, C. (2003) *Journal of Chromatography A* 989, 119.

TABLE U

Bulk characterization after direct capture using A2PS process

| Bulk characterization | Units | Specification | BULK 1<br>7075-035-01 UF2 | BULK 2<br>7075-41-05 UF2 |
|---|---|---|---|---|
| Quantification | | | | |
| Protein content | mg/mL; alpha = 1.26 at 280 nm | | 0.584 | 0.171 |
| RP-HPLC | mg/mL | | 0.586 | 0.141 |
| Product conformity | | | | |
| Isoform profile by IEF/WB | | cluster of bands falls below pI4.6 as in reference | atypique (cluster below pI 3.5)* | atypique (cluster below pI 4.2)* |
| Isoform profile by CZE | % | M0 + M1 < 30% | M0 = 0%<br>M1 = 13.7% | M0 = 0.6%<br>M1 = 10.3% |
| | % | M2 | M2 = 68.6% | M2 = 71.6% |
| | % | M3 | M3 = 17.7% | M3 = 17.5% |
| Product based impurities | | | | |
| Dimers and higher molecular weight (SE-HPLC) | % | | 92.6 | 93.3 |
| Dimers and higher molecular weight (SDS/WB) | % | | Dimers: 8%(28%)<br>Aggregats: 0%(15%) | Dimers: 0%(33%)<br>Aggregats: 0%(n/a) |
| Truncated forms (SDS/WB) | % | | 21% (22%) | 4% (7%) |
| Process based impurities | | | | |
| Cell culture derived protein contaminations (Immunoassay) | ng/mg | | 51 | 69 |
| Residual DNA | | | not performed | not performed |

*atypique IEF/WB profile due to a too selective CM step.
**Value for the starting material

CONCLUSIONS

Table V summarizes the results obtained with traditional chromatographic capture steps shows that A2PS process is simpler; can provide better purity, yield and can be faster.

TABLE V

Process performances comparison between different capture steps applied on IL-18BP

| | Q SFF | Fractogel TMAE HiCap | A2PS |
|---|---|---|---|
| Load condition | UF/DF needed | UF/DF needed | Direct capture |
| Yield | 89% | 91% | 98% |
| Purity (ELISA/Bradford) | 46% | 42% | 72% |
| Run times | 720 min | 360 min | 240 min |

6. Bamberger, S., Brooks, D. E., Sharp, K. A., van Alstine, J. M., & Webber, T. J. (1985) in *Partitioning in Aqueous Two-Phase Systems: Theory, Methods, Uses, and Applications to Biotechnology* (Walter, H., Brooks, D. E., & Fisher, D., Eds.) pp 85 Academic Press, Orlando, Fla.
7. Baskir, J. N., Hatton, T. A., & Sutter, V. W. (1987) *Macromolecules* 20, 1300.
8. Baskir, J. N., Hatton, T. A., & Sutter, V. W. (1989) *Biotechnol. Bioeng.* 34, 541.
9. Bierau, H., Hinton, R. J., & Lyddialt, A. (2001) *Bioseparation*.
10. Bleier, J. E., Kim, E. H., & Chen, X. D. (2001) *Biotechnol. Prog.* 17, 697.
11. Bompensieri, S., Mahler, G. F., Castaneda, N., Miranda, M. V., Cascade, O., & Nude, B. C. (1998) *Biotechnology Techniques* 12, 611.
12. Boschetti, E., Jungbauer, Sep. Sci & Tech. 2 No. 15, Acad. Press (2000) 53

13. Boschetti et al., Genetic Engineering Vol. 20, No. 13, July, 2000
14. Braunstein, E. L., Becker, N. T., anshaw, G., and raycar, T. P. (WO 96/23061). 1995. (to Geneencor International, Inc.).
15. Brewer, J. W., Brothers, C. E., Farver, T. F., im, C. Y., and ee, E. (U.S. Pat. No. 4,728,613). 1988. (to Miles Laboratories, Inc).
16. Builder, S. E., Hart, R. A., Lester, P. M., Ogez, J. R., and Reifsnyder, D. H. (U.S. Pat. No. 5,407,819). 1995. (to Genentech, Inc.).
17. Cordes, A. & Kula, M. R. (1994) *Methods Enzymol* 228, 600.
18. Costa, M. J., Cunha, M. T., Cabral, J. M., & Aires-Barros, M. R. (2000) *Bioseparation* 9, 231.
19. Devereux J et al, Nucleic Acids Res, 12, 387-395, 1984.
20. Diamond, A. D., Yu, K., & Hsu, J. T. (1990) *ACS Symposium Series* 427, 52.
21. Dos Reis Coimbra, J., Thömmes, J., & Kula, M. R. (1994) *Journal of Chromatography A* 668, 85.
22. Dove, G. B and Mitra, G. (U.S. Pat. No. 4,684,723). 1988. (to Miles Laboratories, Inc).
23. Duarte, M., Portugal, E. P., Ponezi, A. N., Bim, M. A., Tagliari, C. V., & Franco, T. T. (1999) *Biorescource Technology* 68, 49.
24. Eitman, M. A. & Gainer, J. L. (1990) *Biotechnol.Prog.* 6, 479.
25. Eitman, M. A. & Gainer, J. L. (1991) *Bioseparation* 2, 31.
26. Enfors, S. O., Kölher, K., Ljundquist, Ch., Nilsson, B., and Veide, A. (WO 92/07868). 1992. (Pharmacia AB, Sweden).
27. Fernandes, S., Kim, H. S., & Hatti-Kaul, R. (2002) *ProteinExpr.Purif.* 24, 460.
28. Grantham et al., Science, Vol. 185, pp. 862-864 (1974)
29. Guan, Y., Wu, S. Y., Treffy, E., & Iley, T. H. (1992) *Biotechnol.Bioeng.* 40, 517.
30. Guiliano, K. A. and Szlag, D. C. (U.S. Pat. No. 5,093,254). 1992. (to the United States).
31. Guinn, M. R. Aqueous two-phase metal affinity partitioning protein purification system. (U.S. Pat. No. 5,907,035). 1997. (to Baxter Biotech Technology Sarl, Neuchatel, CH).
32. Guoqiang, D., Kaul, R., & Mattiasson (1994) *Journal of Chromatography A* 668, 145.
33. Gustafsson, S. J., Hedman, P. O., Ling, T. G. I., and Mattiasson, B. G. (U.S. Pat. No. 4,579,661). 1986. (to Pharmacia AB, Sweden).
34. Hart, R. A., Lester, P. M., Reifsnyder, D. H., Ogez, J. R., & Builder, S. E. (1994) *Biotechnology* (NY) 12, 1113.
35. Hatti-Kaul, R. (2000) in *Aqueous Two-Phase Systems: Methods and Protocols*, Humana Press, Totowa, N.J.
36. Hayenga, K. J., Valax, and P. P. Methods for protein purification using aqueous two-phase extraction. (U.S. Pat. No. 6,437,101). 1999. (to Akzo Nobel N.V., Arnhem, N L).
37. Haynes, C. A., Beynon, R. A., King, R. S., Blanch, H. W., & Prausnitz, J. M. (1989a) *Journal of Physical Chemistry* 93, 5612.
38. Haynes, C. A., Blanch, H. W., & Prausnitz, J. M. (1989b) *Fluid Phase Equilibria* 53, 463.
39. Heinsohne, H. G. and Hayenga, K. J. (EU 0 477284 B1). 1995. (to Smithkline Biologicals).
40. Heinsohne, H. G., Lorch, J. D., and Arnold, R. E. (U.S. Pat. No. 5,139,943). 1992. (to Genecor International, Inc.).
41. Johansson, G. & Reczey, K. (1998) *Journal of Chromatography B* 711, 161.
42. Kim, C. Y., Farver, T. F., and Brewer, J. W. (U.S. Pat. No. 4,508,825). 1985. (to Miles Laboratories, Inc.).
43. Kim S H, Eisenstein M, Reznikov L, Fantuzzi G, Novick D, Rubinstein M, Dinarello C A. Structural requirements of six naturally occurring isoforms of the IL-18 binding protein to inhibit IL-18. Proc Natl Acad Sci USA 2000; 97:1190-1195.
44. King, R. S., Blanch, H. W., & Prausnitz, J. M. (1988) *American Institute of Chemical Engineers Journal* 34, 1585.
45. Kirchberger, J., Kopperschläger, G., Rockstroh, M., and Eisenbrandt, K. (DD 298 424). 1992. (to Universität Leipzig, Germany).
46. Lee, C. J. and Khan, P. (U.S. Pat. No. 5,407,579). 1995. (to National Science Council, Taipei).
47. Li, Y. & Beitle, R. R. (2002) *Biotechnol. Prog.* 18, 1054.
48. Lorch, J. D., Clarkson, E., Larenas, B. S., Bower, B. S, and Weiss, G. L. (U.S. Pat. No. 5,328,841). 1994. (to Genecore International, Inc.).
49. Menge, U., Fraune, E., Lehmann, J., & Kula, M. R. (1987) *Dev Biol Stand* 66, 391.
50. Menge, U., Morr, M., and Kula, M. R. (DE 2943016 C2). 1984. (to the Gesellschaft für Biotechnologische Forschung mbH).
51. Minami, N. M. & Kilikian, B. V. (1997) *Journal of Chromatography* 711, 309.
52. Novick, D, Kim, S-H, Fantuzzi, G, Reznikov, L, Dinarello, C, and Rubinstein, M (1999). Immunity 10, 127-136.
53. Paul, F., Monsan, P., and Auriol, D. (U.S. Pat. No. 4,591,563). 1986. (to Societe Nationale Elf Aquitaine, France).
54. Pearson, Methods Enzymol. 1990; 183:63-98
55. Persson, J., Johasson, H. O., & Tjemeld, F. (1999) *Journal of Chromatography A* 864, 31.
56. J. Porath, J. Carlsson, I. Olsson, and G. Belfrage, Nature (London) 258, 598-599 (1975)
57. J. Porath and B. Olin, Biochemistry 22, 1621-1630 (1983)
58. Puren et al., Proc Natl Acad Sci USA. 1999 Mar. 2; 96(5):2256-61.
59. Schütte, H., Hummel, W., & Kula, M. R. (1984) *Applied Microbiology and Biotechnology* 19, 167.
60. Schütte, H., Hummel, W., Tsai, H., & Kula, M. R. (1985) *Applied Microbiology and Biotechnology* 22, 306.
61. Sieron, R., Wondraczeck, R., Binder, K, Dittmar, H., Lambrecht, K., and Thessa, H. (DD 288837). 1994. (to Zentralinstitut für Mikrobiologie und experimentelle Therapie).
62. Suzuki, M., Kamihira, M., Shiraishi, T., Takeuchi, H., & Kobayashi, T. (1995) *Journal of Fermentation and Bioengineering* 80, 78.
63. Tjemeld, F. & Johansson, G. (1987) *Biotechnol.Bioeng.* 30, 809-816.
64. Tjemeld, F., Persson, J., and Johansson, H. O. Separation method utilizing liquid-liquid partition. (U.S. Pat. No. 6,454,950). 2002. (to Amersham Pharmacia Biotech AB, Uppsala, SE).
65. Urushihara, J Pediatr Surg. 2000 Mar;35(3):446-9.
66. van Wijnendaele, F., Gilles, D., and Simonet, G. (EU 0199698 B1). 1991. (to Smithkline Biologicals S.A.).
67. Vigers et al., Nature. 1997 Mar. 13; 386(6621):190-4.
68. Walter, H., Brooks, D. E., & Fisher, D. (1985) in *Partitioning in Aqueous Two-Phase Systems Theory, Methods, Uses, and Applications to Biotechnology*, Academic Press, Orlando, Fla.
69. Zaslavsky, B. Y. (1995b) in *Aqueous Two-Phase Partitioning* (Zaslavsky, B. Y., Ed.) pp 503-667, Marcel Dekker, Inc, New York, Basel, Honk Hong.

70. Zaslavsky, B. Y. (1995a) in *Aqueous Two-Phase Partitioning* (Zaslavsky, B. Y., Ed.) pp 75-152, Marcel Dekker, Inc, New York, Basel, Honk Hong.

The invention claimed is:

1. A process for purifying interleukin-18 binding protein (IL-18BP) from a fluid comprising at least one step using aqueous two-phase partitioning that comprises a polyethylene glycol (PEG) phase and a $(Na_2)SO_4$ salt phase, wherein the concentrations of PEG and $(Na)_2SO_4$ in the two phases are calculated according to the following formula:

$$y=-2.5108x+35.159 \qquad \text{a)}$$

wherein y=PEG in % [w/w] and x=$(Na_2)SO_4$ in % [w/w];

$$y=-2.5573x+35.757 \qquad \text{b)}$$

wherein y=PEG in % [w/w] and x=$(Na_2)SO_4$ in % [w/w]; or $$y=-2.1182x+35.355 \qquad \text{c)}$$

wherein y =PEG in % [w/w] and x=$(Na_2)SO_4$ in % [w/w].

2. The process according to claim 1, wherein the PEG has a molecular weight ranging between about 2000 and about 12000.

3. The process according to claim 1, wherein the PEG has a molecular weight of about 10000.

4. The process according to claim 1, wherein the concentrations of PEG and $(Na)_2SO_4$ in the two phases are calculated according to the following formula: y=-2.5108x+35.159, wherein y=PEG in % [w/w] and x=$(Na_2)SO_4$ in % [w/w].

5. The process according to claim 1, wherein the concentrations of PEG and $(Na)_2SO_4$ in the two phases are calculated according to the following formula: y=-2.5573x+35.757, wherein y=PEG in % [w/w] and x=$(Na_2)SO_4$ in % [w/w].

6. The process according to claim 1, wherein the concentrations of PEG and $(Na)_2SO_4$ in the two phases are calculated according to the following formula: y=-2.1182x+35.355, wherein y=PEG in % [w/w] and x=$(Na_2)SO_4$ in % [w/w].

7. A process for purifying interleukin-18 binding protein (IL-18BP) from a fluid comprising at least one step using aqueous two-phase partitioning that comprises a polyethylene glycol (PEG) phase and a $(Na_2)SO_4$ salt phase, wherein the concentration of the PEG phase ranges from about 21% to about 29% (w/w) and the concentration of $(Na_2)SO_4$ ranges from about 1.9% to about 5.5% (w/w).

8. The process according to claim 7, wherein said process is performed at a pH of about 5, a PEG concentration of about 28.6% and a $(Na_2)SO_4$ concentration of about 1.9%.

9. The process according to claim 7, wherein said process is performed at a pH of about 5, a PEG concentration of about 27.9% and a $(Na_2)$ $SO_4$ concentration of about 2.8 %.

10. The process according to claim 7, wherein said process is performed at a pH of about 7, a PEG concentration of about 28.75% and a $(Na_2)SO_4$ concentration of about 2.25%.

11. The process according to claim 7, wherein said process is performed at a pH of about 7, a PEG concentration of about 21% and a $(Na_2)SO_4$ concentration of about 5.5%.

12. The process according to claim 7, wherein the PEG has a molecular weight ranging between about 2000 and about 12000.

13. The process according to claim 7, wherein the PEG has a molecular weight of about 10000.

14. The process according to claim 7, wherein said process is performed at a pH of 5, a PEG concentration of 28.6% and a $(Na_2)SO_4$ concentration of 1.9%.

15. The process according to claim 7, wherein said process is performed at a pH of 5, a PEG concentration of 27.9% and a $(Na_2)SO_4$ concentration of 2.8%.

16. The process according to claim 7, wherein said process is performed at a pH of 7, a PEG concentration of 28.75% and a $(Na_2)SO_4$ concentration of 2.25%.

17. The process according to claim 7, wherein said process is performed at a pH of 7, a PEG concentration of 21% and a $(Na_2)SO_4$ concentration of 5.5%.

* * * * *

UNITED STATES PATENT AND TRADEMARK OFFICE
CERTIFICATE OF CORRECTION

PATENT NO. : 7,439,336 B2
APPLICATION NO. : 11/630845
DATED : October 21, 2008
INVENTOR(S) : Henri Kornmann and Gianni Baer It is certified that error appears in the above-identified patent and that said Letters Patent is hereby corrected as shown below:

Column 3,
Line 8, "bimodal line. The bimodal curve" should read
--binodal line. The binodal curve--.

Column 5,
Line 44, "Tran membrane" should read --transmembrane--.
Line 51, "(hill-18BP)" should read --(hIL-18BP)--.

Column 8,
Line 10, "legend" should read --ligand--.
Line 16, "sparse" should read --sepharose--.
Line 22, "phenyl-sparse (agars)" should read --phenyl-sepharose (agarose)--.
Line 32, "elate" should read --eluate--.
Line 37, "elate" should read --eluate--.
Lines 39-40, "defloration" should read --diafiltration--.
Line 44, "sparse" should read --sepharose--.
Line 45, "sparse" should read --sepharose--.
Line 46, "cheated" should read --chelated--.
Line 67, "Phenyl-Sepahrose" should read --Phenyl-Sepharose--.

Column 9,
Line 2, "soleplate" should read --sulphate--.
Line 6, "soleplate" should read --sulphate--.
Line 55, "unqualified" should read --unclarified--.
Lines 59-60, "unqualified" should read --unclarified--.

Column 10,
Line 36, "produced recombinant" should read --produced recombinantly--.

Column 11,
Line 38, "mute in" should read --mutein--.
Line 42, "mute in" should read --mutein--.
Line 47, "mute in" should read --mutein--.
Line 52, "mute in" should read --mutein--.

Column 12,
Line 12, "cytokine residues" should read --cysteine residues--.

UNITED STATES PATENT AND TRADEMARK OFFICE
CERTIFICATE OF CORRECTION

PATENT NO. : 7,439,336 B2
APPLICATION NO. : 11/630845
DATED : October 21, 2008
INVENTOR(S) : Henri Kornmann and Gianni Baer It is certified that error appears in the above-identified patent and that said Letters Patent is hereby corrected as shown below:

Column 14,
Line 46, "tripe tide" should read --tripeptide--.
Line 64, "multimedia" should read --multimeric--.

Column 15,
Line 3, " >70" should read -->70%--.
Line 4, "of dimmers" should read --of dimers--.
Line 5, "no dimmers" should read --no dimers--.
Line 25, "pertinacious" should read --proteinaceous--.
Line 35, "recipients" should read --excipients--.
Line 40, "potential" should read --parenteral--.
Line 47, "transversal" should read --transdermal--.
Line 58, "recipients" should read --excipients--.
Line 60, "potential" should read --parenteral--.
Line 63, "potential" should read --parenteral--.
Line 65, "is tonicity" should read --isotonicity--.

Column 16,
Line 10, "catatonic" should read --cytotoxic--.

Column 18,
Line 12, "$2^{5-1}$" should read --$2^{5"1}$--.

Column 28,
Lines 62-63, "pupating" should read --pipetting--.

Column 30,
Line 63, "Due the high" should read --Due to the high--.
Lines 64-65, "isoforms" Isoforms" should read --isoforms". Isoforms--.
Line 66, "isoforms" Isoforms" should read --isoforms". Isoforms--.

Column 31,
Line 15, "showed above" should read --shown above--.

Column 32,
Line 62, "(Fluka° 37429-1EA)" should read --(Fluka 37429-1EA)--.

UNITED STATES PATENT AND TRADEMARK OFFICE
CERTIFICATE OF CORRECTION

PATENT NO. : 7,439,336 B2
APPLICATION NO. : 11/630845
DATED : October 21, 2008
INVENTOR(S) : Henri Kornmann and Gianni Baer It is certified that error appears in the above-identified patent and that said Letters Patent is hereby corrected as shown below:

<u>Column 36,</u>
Line 3, "Person, J., and Tjemeld, F." should read --Persson, J., and Tjerneld, F.--.
Line 64, "Nude, B.C." should read --Nudel, B.C.--.

<u>Column 37,</u>
Line 3, "anshaw, G., and raycar, T. P." should read --Anshaw, G., and Raycar, T. P.--.
Line 4, "Geneencor" should read --Genencor--.
Lines 6-7, "im, C.Y., and ee, E." should read --Kim, C.Y., and Lee, E.--.
Line 52, "Valax, and P.P." should read --and Valax, P.P.--.

<u>Column 38,</u>
Line 20, "(DE 2943016 C2)" should read --(DE 2943026 C2)--.
Line 32, "Tjemeld, F." should read --Tjerneld, F.--.
Line 51, "Tjemeld, F." should read --Tjerneld, F.--.
Line 53, "Tjemeld, F." should read --Tjerneld, F.--.

Signed and Sealed this

Seventeenth Day of March, 2009

JOHN DOLL
*Acting Director of the United States Patent and Trademark Office*